(12) United States Patent
Polisetti et al.

(10) Patent No.: US 8,927,549 B2
(45) Date of Patent: Jan. 6, 2015

(54) ADAMANTYL BENZAMIDE DERIVATIVES

(75) Inventors: Dharma Rao Polisetti, High Point, NC (US); Suparna Gupta, Greensboro, NC (US); Soren Ebdrup, Roskilde (DK)

(73) Assignee: High Point Pharmaceuticals, LLC, High Point, NC (US)

( * ) Notice: Subject to any disclaimer, the term of this patent is extended or adjusted under 35 U.S.C. 154(b) by 0 days.

(21) Appl. No.: 13/128,045

(22) PCT Filed: Nov. 17, 2009

(86) PCT No.: PCT/US2009/064776
§ 371 (c)(1),
(2), (4) Date: May 6, 2011

(87) PCT Pub. No.: WO2010/059618
PCT Pub. Date: May 27, 2010

(65) Prior Publication Data
US 2011/0224244 A1    Sep. 15, 2011

Related U.S. Application Data

(60) Provisional application No. 61/116,810, filed on Nov. 21, 2008.

(51) Int. Cl.
| | | |
|---|---|---|
| C07D 213/89 | (2006.01) |
| A61K 31/44 | (2006.01) |
| C07D 237/12 | (2006.01) |
| A61K 31/50 | (2006.01) |
| C07D 239/42 | (2006.01) |
| A61K 31/505 | (2006.01) |
| A61P 9/12 | (2006.01) |
| A61P 9/00 | (2006.01) |
| A61P 3/10 | (2006.01) |
| A61P 3/04 | (2006.01) |

(52) U.S. Cl.
USPC .......... 514/247; 514/345; 514/275; 544/241; 544/294; 546/285

(58) Field of Classification Search
USPC ............. 514/247, 345, 275; 544/241, 294; 546/285
See application file for complete search history.

(56) References Cited

U.S. PATENT DOCUMENTS

| | | | |
|---|---|---|---|
| 4,851,423 A | 7/1989 | Girijavallabhan et al. |
| 4,963,590 A | 10/1990 | Backstrom et al. |
| 5,049,695 A | 9/1991 | Abraham et al. |
| 5,112,861 A | 5/1992 | Backstrom et al. |
| 5,122,539 A | 6/1992 | Abraham et al. |
| 5,258,407 A | 11/1993 | Washburn et al. |
| 5,260,325 A | 11/1993 | Markwalder et al. |
| 5,272,167 A | 12/1993 | Girijavallabhan et al. |
| 5,290,803 A | 3/1994 | Abraham et al. |
| 5,314,880 A | 5/1994 | Whittaker et al. |
| 5,382,680 A | 1/1995 | Abraham et al. |
| 5,432,191 A | 7/1995 | Abraham et al. |
| 5,446,194 A | 8/1995 | Backstrom et al. |
| 5,459,144 A | 10/1995 | Girijavallabhan et al. |
| 5,585,394 A | 12/1996 | Di Malta et al. |
| 5,591,892 A | 1/1997 | Abraham et al. |
| 5,596,020 A | 1/1997 | Morris et al. |
| 5,648,375 A | 7/1997 | Abraham et al. |
| 5,677,330 A | 10/1997 | Abraham et al. |
| 5,705,521 A | 1/1998 | Abraham et al. |
| 5,731,454 A | 3/1998 | Abraham et al. |
| 5,750,532 A | 5/1998 | Girijavallabhan et al. |
| 5,786,379 A | 7/1998 | Bernardon |
| 5,795,907 A | 8/1998 | Kalindjian et al. |
| 5,872,282 A | 2/1999 | Abraham et al. |
| 5,912,260 A | 6/1999 | Kalindjian et al. |
| 5,919,829 A | 7/1999 | Kalindjian et al. |
| 5,927,283 A | 7/1999 | Abraham et al. |
| 5,939,437 A | 8/1999 | Kalindjian et al. |
| 6,001,879 A | 12/1999 | Seitz et al. |
| 6,458,803 B1 | 10/2002 | Sikorski et al. |
| 6,548,549 B1 | 4/2003 | Seitz et al. |
| 6,613,803 B1 | 9/2003 | Wang et al. |
| 6,638,947 B2 | 10/2003 | Wang et al. |
| 6,696,442 B2 | 2/2004 | Wang et al. |
| 6,833,371 B2 | 12/2004 | Atkinson et al. |
| 7,129,242 B2 | 10/2006 | Satoh et al. |
| 7,358,238 B2 | 4/2008 | Andersen et al. |
| 7,501,405 B2 | 3/2009 | Kampen et al. |
| 7,700,583 B2 | 4/2010 | Gundertofte et al. |
| 7,723,323 B2 | 5/2010 | Andersen et al. |
| 8,048,908 B2 | 11/2011 | Ebdrup et al. |
| 8,053,431 B2 | 11/2011 | Kilburn et al. |

(Continued)

FOREIGN PATENT DOCUMENTS

| | | |
|---|---|---|
| CN | 1736485 | 2/2006 |
| JP | 08-048662 | 2/1996 |

(Continued)

OTHER PUBLICATIONS

Rauz, et al., Q. J. Med., 2003; 96:481-490.*
Tomlinson, et al., Endocrine Reviews, Oct. 2004, 25(5):831-866.*
Andrew et al., J. Clin. Endocrinol. Metab. vol. 87, pp. 277-285 (2002).
Andrews et al., J. Clin. Endocrinol. Metab. vol. 88, pp. 285-291 (2003).
Barf T et al: "Recent progress in 11-[beta]-hydroxysteroid dehydrogenase type 1 (11-[beta]-HSD1) inhibitor development" Drugs of the Future 2006 Spain, vol. 31, No. 3, Mar. 2006, pp. 231-243.
Bird et al., J. Physiology vol. 585, pp. 187-201 (2007).

(Continued)

*Primary Examiner* — Susanna Moore
*Assistant Examiner* — Cecilia M Jaisle
(74) *Attorney, Agent, or Firm* — Samuel B. Rollins

(57) ABSTRACT

Embodiments of the present invention provide adamantyl benzamide derivatives and pharmaceutical compositions comprising adamantyl benzamide derivatives. Methods of use of such compounds and compositions to modulate the activity of 11β-hydroxysteroid dehydrogenase type 1 (11βHSD1) in a subject are also provided.

63 Claims, No Drawings

(56) References Cited

U.S. PATENT DOCUMENTS

| | | | |
|---|---|---|---|
| 8,053,447 | B2 | 11/2011 | Ebdrup et al. |
| 8,138,342 | B2 | 3/2012 | Kilburn et al. |
| 8,153,798 | B2 | 4/2012 | Kilburn et al. |
| 2005/0054850 | A1 | 3/2005 | Wu et al. |
| 2005/0154202 | A1 | 7/2005 | Hagmann et al. |
| 2005/0261302 | A1 | 11/2005 | Hoff et al. |
| 2006/0079506 | A1 | 4/2006 | Linders et al. |
| 2006/0094699 | A1 | 5/2006 | Kampen et al. |
| 2006/0111366 | A1 | 5/2006 | Andersen et al. |
| 2006/0149070 | A1 | 7/2006 | Rohde et al. |
| 2006/0281773 | A1 | 12/2006 | Patel et al. |
| 2007/0270408 | A1 | 11/2007 | Andersen et al. |
| 2008/0108598 | A1 | 5/2008 | Andersen et al. |
| 2009/0105289 | A1 | 4/2009 | Kilburn et al. |
| 2009/0118259 | A1 | 5/2009 | Kilburn et al. |
| 2009/0124598 | A1 | 5/2009 | Andersen et al. |
| 2009/0137574 | A1 | 5/2009 | Kampen et al. |
| 2009/0264412 | A1 | 10/2009 | Kampen et al. |
| 2009/0264414 | A1 | 10/2009 | Andersen et al. |
| 2009/0306048 | A1 | 12/2009 | Kilburn et al. |
| 2009/0325932 | A1 | 12/2009 | Ebdrup et al. |
| 2010/0056600 | A1 | 3/2010 | Ebdrup et al. |
| 2010/0076041 | A1 | 3/2010 | Kilburn et al. |
| 2010/0087543 | A1 | 4/2010 | Ebdrup et al. |
| 2010/0120743 | A1 | 5/2010 | Gundertofte et al. |
| 2010/0137377 | A1 | 6/2010 | Petersen et al. |
| 2010/0168083 | A1 | 7/2010 | Ebdrup |
| 2010/0197658 | A1 | 8/2010 | Andersen et al. |
| 2010/0292215 | A1 | 11/2010 | Ebdrup et al. |
| 2010/0331366 | A1 | 12/2010 | Ebdrup |
| 2011/0003852 | A1 | 1/2011 | Ebdrup |
| 2011/0003856 | A1 | 1/2011 | Ebdrup |
| 2011/0039853 | A1 | 2/2011 | Ebdrup |
| 2011/0224244 | A1 | 9/2011 | Polisetti et al. |
| 2011/0312949 | A1 | 12/2011 | Ebdrup |
| 2012/0004209 | A1 | 1/2012 | Ebdrup et al. |
| 2012/0010194 | A1 | 1/2012 | Ebdrup et al. |
| 2012/0029029 | A1 | 2/2012 | Polisetti et al. |

FOREIGN PATENT DOCUMENTS

| | | |
|---|---|---|
| JP | 2007-231005 | 9/2007 |
| WO | WO 97/07789 | 3/1997 |
| WO | WO 97/22588 | 6/1997 |
| WO | WO 97/24328 | 7/1997 |
| WO | WO 00/63165 | 10/2000 |
| WO | WO 00/73283 | 12/2000 |
| WO | WO 01/90090 | 11/2001 |
| WO | WO 01/90091 | 11/2001 |
| WO | WO 01/90092 | 11/2001 |
| WO | WO 01/90093 | 11/2001 |
| WO | WO 01/90094 | 11/2001 |
| WO | WO 02/02797 | 1/2002 |
| WO | WO 02/072084 | 9/2002 |
| WO | WO 02/076435 | 10/2002 |
| WO | WO 03/065983 | 8/2003 |
| WO | WO 03/070732 | 8/2003 |
| WO | WO 03/086410 | 10/2003 |
| WO | WO 2004/033427 | 4/2004 |
| WO | WO 2004/052461 | 6/2004 |
| WO | WO 2004/056744 | 7/2004 |
| WO | WO 2004/056745 | 7/2004 |
| WO | WO 2006/044645 | 7/2004 |
| WO | WO 2004/065351 | 8/2004 |
| WO | WO 2004/087159 | 10/2004 |
| WO | WO 2004/089380 | 10/2004 |
| WO | WO 2004/089415 | 10/2004 |
| WO | WO 2004/089416 | 10/2004 |
| WO | WO 2004/089470 | 10/2004 |
| WO | WO 2004/089471 | 10/2004 |
| WO | WO 2004/089896 | 10/2004 |
| WO | WO 2005/013950 | 2/2005 |
| WO | WO 2005/085202 | 9/2005 |
| WO | WO 2006/014012 | 2/2006 |
| WO | WO 2006/028958 | 3/2006 |
| WO | WO 2006/040329 | 4/2006 |
| WO | WO 2006/048330 | 5/2006 |
| WO | WO 2006/055752 | 5/2006 |
| WO | WO 2006/094633 | 9/2006 |
| WO | WO 2006/105127 | 10/2006 |
| WO | WO 2006/113261 | 10/2006 |
| WO | WO 2007/051810 | 5/2007 |
| WO | WO 2007/051811 | 5/2007 |
| WO | WO 2007/058960 | 5/2007 |
| WO | WO 2007/066784 | 6/2007 |
| WO | WO 2007/107550 | 9/2007 |
| WO | WO 2007/109160 | 9/2007 |
| WO | WO 2007/115935 | 10/2007 |
| WO | WO 2007/144394 | 12/2007 |
| WO | WO 2008/006702 | 1/2008 |
| WO | WO 2008/006703 | 1/2008 |
| WO | WO 2008101914 | * 2/2008 |
| WO | WO 2008127924 | * 4/2008 |
| WO | WO 2008/101885 | 8/2008 |
| WO | WO 2008/101886 | 8/2008 |
| WO | WO 2008/101907 | 8/2008 |
| WO | WO 2008/101914 | 8/2008 |
| WO | WO 2008/110196 | 9/2008 |
| WO | WO 2008/119017 | 10/2008 |
| WO | WO 2008/127924 | 10/2008 |
| WO | WO 2008/134221 | 11/2008 |
| WO | WO 2009/126863 | 10/2009 |
| WO | WO 2010/057126 | 5/2010 |
| WO | WO 2012/015715 | 2/2012 |

OTHER PUBLICATIONS

Brem et al., Hypertension vol. 31, pp. 459-462 (1998).
Brindley et al., Progress Lipid Res. vol. 30, pp. 349-360 (1991).
Bujalska et al., Endocrinology vol. 140, pp. 3188-3196 (1999).
Carruthers et al., J. Chem. Soc. Perkin Trans. 1 vol. 10, pp. 2854-2856 (1990).
Cooper et al., Bone vol. 27, pp. 375-381 (2000).
Coppola, Gary M. et al., "Perhydroquinolylbenzamides as Novel Inhibitors of 11.beta.-Hydroxysteroid Dehydrogenase Type 1" Journal of Medicinal Chemistry, 48 (21), 6696-6712 Coden: Jmcmar; ISSN: 0022-2623, 2005.
Davani et al., J. Biol. Chem. vol. 275, pp. 34841-34844 (2000).
European Search Report for European Patent Application No. 09828106.6 dated Jul. 30, 2012.
Evans et al., J. Med. Chem. vol. 35, pp. 3919-3927 (1992).
Fotsch C. et al., "11 [beta]-Hydroxysteroid dehydrogenase-1 as a therapeutic target for metabolic diseases" Expert Opinion on Therapeutic Patents, Ashley Publications, GB, vol. 15, No. 3, 2005, pp. 289-303.
Hosfield et al., J. Biol. Chem. vol. 280, pp. 4639-4648 (2005).
Ignatova et al., American Journal of Physiology—Endocrinology and Metabolism, 296(2):E367-E377 (2009).
International Preliminary Report on Patentability and Written Opinion for Application No. PCT/EP2008/051971, mailed Sep. 3, 2009.
International Preliminary Report on Patentability for PCT Application No. PCT/US09/64776 mailed Jun. 3, 2011.
International Search Report and Written Opinion for PCT Application No. PCT/US09/04776 mailed Feb. 12, 2010.
International Search Report for Application No. PCT/EP2008/051971, mailed Nov. 6, 2008.
Johnson et al., J. Org. Chem. vol. 35, pp. 622-626 (1970).
Koteletsev et al., Proc. Nat'l Acad. Sci. vol. 94, pp. 14924-14929 (1997).
Mariani et al., Farmaco vol. 38, pp. 653-663 (1983).
Masuzaki et al., J. Clin. Invest. vol. 112, pp. 83-90 (2003).
Masuzaki et al., Science vol. 294, pp. 2166-2170 (2001).
Moisan et al., Endocrinology, vol. 127, pp. 1450-1455 (1990).
Morton et al., J. Biol. Chem. vol. 276, pp. 41293-41300 (2001).
Nankervis et al.: "Calcium sensitizazion as a positive inotropic mechanism . . . " Journal of Cardiovascular Pharmacology, vol. 24, No. 4, 1994, pp. 612-617.
Office Action for related Chinese Patent Application No. 200980146208.1 dated Nov. 1, 2012.
Pending Claims for U.S. Appl. No. 12/092,230, filed Mar. 25, 2011.

(56) References Cited

OTHER PUBLICATIONS

Pending Claims for U.S. Appl. No. 12/293,709, filed Mar. 25, 2011.
Pending Claims for U.S. Appl. No. 12/308,000, filed Mar. 28, 2011.
Pending Claims for U.S. Appl. No. 12/528,227, filed Mar. 28, 2011.
Pending Claims for U.S. Appl. No. 12/528,229, filed Mar. 29, 2011.
Pending Claims for U.S. Appl. No. 12/528,231, filed Mar. 28, 2011.
Pending Claims for U.S. Appl. No. 12/528,233, filed Mar. 29, 2011.
Pending Claims for U.S. Appl. No. 12/595,310, filed Mar. 29, 2011.
Pending Claims for U.S. Appl. No. 12/597,129, filed Mar. 29, 2011.
Pending Claims for U.S. Appl. No. 13/189,640, filed Jul. 25, 2011.
Pending Claims for U.S. Appl. No. 13/220,843, filed Aug. 30, 2011.
Pending Claims for U.S. Appl. No. 13/235,200, filed Sep. 16, 2011.
Rauz et al., Invest. Opthalmol. Vis. Sci. vol. 42, pp. 2037-2042 (2001).
Reed et al., Scand. J. Gastroentreol. vol. 15, pp. 51-56 (1980).
Restriction Requirement for U.S. Appl. No. 12/595,310 dated Jan. 27, 2012.
Rohde et al., "Discovery and Metabolic Stabilization of Potent and Selective 2-Amino-N-(Adamant-2-yl) Acetamine 11beta-Hydroxysteroid Dehydrogenase Type 1 Inhibitors," Journal of Medicinal Chemistry, American Chemical Society, US, 50(1):149-164 (2006).
Schwartz et al., Nature vol. 404, pp. 661-671 (2000).
Sohar R et al: "Conformational Analysis of N-Acylazabycyclooctanes," Magnetic Resonance in Chemistry, John Wiley, Chichester, GB, vol. 23, No. 7, Jan. 1, 1985, pp. 506-513.
Sorensen et al., "Adamantane 11-beta-HSD-1 Inhibitors: Application of an Isocyanide Multicomponent Reaction," Bioorganic & Medicinal Chemistry Letters, Pergamon, Elsevier Science, GB, 16(23): 5958-5962 (2006).
Souness et al., Steroids vol. 67, pp. 195-201 (2002).
Tannin et al., J. Biol. Chem. vol. 266, pp. 16653-16658 (1991).
Tomlinson et al., J. Clin. Endocrinol. Metab. vol. 87, pp. 57-62 (2002).
Villani, F.J. et al.; "Derivatives of 2-Azabicyclo[2.2.2]octane" Journal of Medicinal Chemistry, 1966, pp. 264-265.
Walker et al., J. Clin. Endocrinol. Metab. vol. 80, pp. 3155-3159 (1995).
Whitworth et al., J. Hypertens. vol. 20, pp. 1035-1043 (2002).
Whorwood et al., J. Clin. Endocrinol. Metab. vol. 86, pp. 2296-2308 (2001).
Yau et al., Proc. Nat'l Acad. Sci. vol. 98, pp. 4716-4721 (2001).
Yudt et al., Mol. Endocrinol. vol. 16, pp. 1719-1726 (2002).
Examination Report issued Feb. 7, 2014 corresponding to Australian Patent Application No. 2009316802.
Geluk et al., "Hydride Transfer Reactions of the Adamantyl Cation-II : Synthesis of 1,3- and 1,4-Disubstituted Adamantanes," Tetrahedron, vol. 24, pp. 5369-5377 (1968).

* cited by examiner

ADAMANTYL BENZAMIDE DERIVATIVES

STATEMENT OF RELATED APPLICATIONS

The present application is the U.S. national stage application, pursuant to 35 U.S.C. §371, of international application No. PCT/US2009/064776, filed Nov. 17, 2009, which claims the benefit of priority of U.S. Provisional Patent Application No. 61/116,810, filed Nov. 21, 2008, the contents of which are herein incorporated by reference in their entirety.

FIELD OF THE INVENTION

The present invention relates to substituted adamantyl based inhibitors, to their use in therapy, to pharmaceutical compositions comprising the compounds, to the use of said compounds in the manufacture of medicaments, and to therapeutic methods comprising the administration of said compounds. The present compounds modulate the activity of 11β-hydroxysteroid dehydrogenase type 1 (11βHSD1) and are accordingly useful in the treatment of diseases in which such a modulation is beneficial.

BACKGROUND OF THE INVENTION

Metabolic syndrome is a major global health problem. In the US, the prevalence in the adult population is currently estimated to be approximately 25%, and it continues to increase both in the US and worldwide. Metabolic syndrome is characterized by a combination of insulin resistance, dyslipidemia, obesity and hypertension leading to increased morbidity and mortality of cardiovascular diseases. People with metabolic syndrome are at increased risk of developing frank type 2 diabetes, the prevalence of which is equally escalating.

In type 2 diabetes, obesity and dyslipidemia are also highly prevalent and around 70% of people with type 2 diabetes additionally have hypertension once again leading to increased mortality of cardiovascular diseases.

In the clinical setting, it has long been known that glucocorticoids are able to induce all of the cardinal features of the metabolic syndrome and type 2 diabetes.

11β-hydroxysteroid dehydrogenase type 1 (11βHSD1) catalyzes the local generation of active glucocorticoid in several tissues and organs including predominantly the liver and adipose tissue, but also e.g. skeletal muscle, bone, pancreas, endothelium, ocular tissue and certain parts of the central nervous system. Thus, 11βHSD1 serves as a local regulator of glucocorticoid actions in the tissues and organs where it is expressed.

The role of 11βHSD1 in metabolic syndrome and type 2 diabetes is supported by several lines of evidence. In humans, treatment with the non-specific 11βHSD1 inhibitor carbenoxolone improves insulin sensitivity in lean healthy volunteers and people with type 2 diabetes. Likewise, 11βHSD1 knock-out mice are resistant to insulin resistance induced by obesity and stress. Additionally, the knock-out mice present with an anti-atherogenic lipid profile of decreased VLDL triglycerides and increased HDL-cholesterol. Conversely, mice that overexpress 11βHSD1 in adipocytes develop insulin resistance, hyperlipidemia and visceral obesity, a phenotype that resembles the human metabolic syndrome.

The more mechanistic aspects of 11βHSD1 modulation, and thereby modulation of intracellular levels of active glucocorticoid, have been investigated in several rodent models and different cellular systems. 11βHSD1 promotes the features of the metabolic syndrome by increasing hepatic expression of the rate-limiting enzymes in gluconeogenesis, namely phosphoenolpyuvate carboxykinase and glucose-6-phosphatase, promoting the differentiation of preadipocytes into adipocytes thus facilitating obesity, directly and indirectly stimulating hepatic VLDL secretion, decreasing hepatic LDL uptake and increasing vessel contractility.

WO 01/90090, WO 01/90091, WO 01/90092, WO 01/90093 and WO 01/90094 disclose various thiazol-sulfonamides as inhibitors of the human 11β-hydroxysteroid dehydrogenase type 1 enzyme, and further state that said compounds may be useful in treating diabetes, obesity, glaucoma, osteoporosis, cognitive disorders, immune disorders and depression. WO 2004/089470 discloses various substituted amides and the use thereof for stimulating 11β-hydroxysteroid dehydrogenase type 1. WO 2004/089415 and WO 2004/089416 disclose various combination therapies using an 11β-hydroxysteroid dehydrogenase type 1 inhibitor and respectively a glucocorticoid receptor agonist or an antihypertensive agent.

As can be seen, there is a need for new compounds that modulate the activity of 11βHSD1 leading to altered intracellular concentrations of active glucocorticoid. More specifically, there is a need for compounds that inhibit the activity of 11βHSD1 leading to decreased intracellular concentrations of active glucocorticoid. Such compounds can be used to treat disorders where a decreased level of active intracellular glucocorticoid is desirable, such as e.g. the metabolic syndrome, type 2 diabetes, impaired glucose tolerance (IGT), impaired fasting glucose (IFG), dyslipidemia, obesity, hypertension, diabetic late complications, cardiovascular diseases, arteriosclerosis, atherosclerosis, myopathy, muscle wasting, osteoporosis, neurodegenerative and psychiatric disorders, and adverse effects of treatment or therapy with glucocorticoid receptor agonists.

SUMMARY OF INVENTION

The present invention provides adamantyl benzamide derivatives as described herein.

In another embodiment, the present invention also provides methods for the preparation of adamantyl benzamide derivatives.

In another embodiment, the present invention provides methods for the preparation of hydroxyadamantylamine derivatives useful as intermediates for the synthesis of chemical compounds, including the admantyl benzamide derivatives according to an embodiment of the present invention.

The present invention also provides pharmaceutical compositions comprising an adamantyl benzamide derivative.

In another embodiment, the present invention provides methods for the preparation of pharmaceutical compositions comprising an adamantyl benzamide derivative. The pharmaceutical compositions may further comprise a pharmaceutically acceptable carrier, excipient, diluent, or mixture thereof.

In another embodiment, the present invention provides methods for the use of adamantyl benzamide derivatives and for the use of pharmaceutical compositions comprising adamantyl benzamide derivatives. The compounds and pharmaceutical compositions of the present invention may be used for the treatment of human or animal disorders.

Additional features of the present invention will be described hereinafter. It is to be understood that the invention is not limited in its application to the details set forth in the foregoing or following description but is capable of other embodiments and of being practiced or carried out in various ways.

DETAILED DESCRIPTION

The invention provides for a compound of the general formula (I):

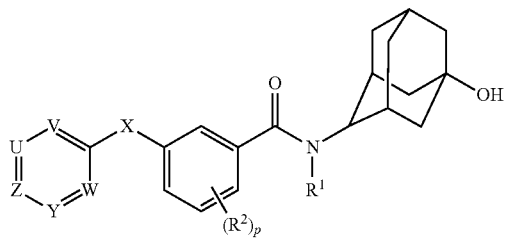

(I)

wherein
R¹ is selected from the group consisting of hydrogen, —C₁-C₈ alkyl, and —C₁-C₆ alkylene-aryl;
R² is each independently $R^a$;
U is =N— or =C(R³)—;
V is =N— or =C(R⁴)—;
W is =N— or =C(R⁵)—;
Y is =N— or =C(R⁶)—;
Z is =N— or =C(R⁷)—;
provided that one or two of U, V, W, Y and Z are =N—;
wherein R³, R⁴, R⁵, R⁶ and R⁷ are each independently $R^b$;
X is selected from the group consisting of —N(H)—, —O—, —S—, —S(O)— and —S(O₂)—;
$R^a$ and $R^b$ are each independently selected from the group consisting of halogen, cyano, —COOR⁸ and —R⁹-L-R¹⁰;
R⁸ is selected from the group consisting of hydrogen, —C₁-C₆alkyl, —C₁-C₆alkyleneoxy-C₁-C₆alkyl, —C₃-C₁₀cycloalkyl, aryl and —C₁-C₆alkylene-aryl, wherein the aryl group is optionally substituted with one or more R¹¹;
R⁹ is either a direct bond or a divalent radical selected from the group consisting of C₁-C₆ alkylene, C₃-C₁₀cycloalkylene and arylene, wherein the arylene group is optionally substituted with one or more R¹¹;
R¹⁰ is selected from the group consisting of hydrogen, —C₁-C₆alkyl, —C₃-C₁₀cycloalkyl, haloalkyl, trihaloalkyl and aryl, wherein the aryl group is optionally substituted with one or more R¹¹;
L is a direct bond, —O— or —S—;
R¹¹ is halogen, hydroxy, —C₁-C₆alkyl, aryl, hetaryl, —C₃-C₁₀cycloalkyl, and —C₃-C₁₀hetcycloalkyl;
p is 0, 1, 2, 3 or 4; or
a pharmaceutically acceptable salt thereof.

While not limited thereto, the foregoing represents specific embodiments of the present invention.

Embodiment 1: In a first embodiment, the present invention provides for a compound of the general formula (I):

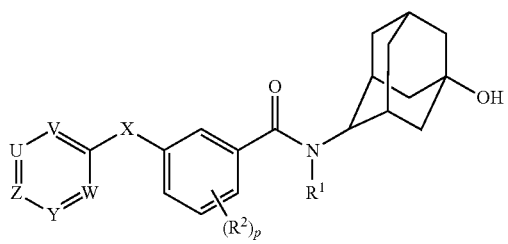

(I)

wherein
R¹ is selected from the group consisting of hydrogen, —C₁-C₈ alkyl, and —C₁-C₆ alkylene-aryl;
R² is each independently $R^a$;
U is =N— or =C(R³)—;
V is =N— or =C(R⁴)—;
W is =N— or =C(R⁵)—;
Y is =N— or =C(R⁶)—;
Z is =N— or =C(R⁷)—;
provided that one or two of U, V, W, Y and Z are =N—;
wherein R³, R⁴, R⁵, R⁶ and R⁷ are each independently $R^b$;
X is selected from the group consisting of —N(H)—, —O—, —S—, —S(O)— and —S(O₂)—;
$R^a$ and $R^b$ are each independently selected from the group consisting of halogen, cyano, —COOR⁸ and —R⁹-L-R¹⁰;
R⁸ is selected from the group consisting of hydrogen, —C₁-C₆alkyl, —C₁-C₆alkyleneoxy-C₁-C₆alkyl, —C₃-C₁₀cycloalkyl, aryl and —C₁-C₆alkylene-aryl, wherein the aryl group is optionally substituted with one or more R¹¹;
R⁹ is either a direct bond or a divalent radical selected from the group consisting of C₁-C₆ alkylene, C₃-C₁₀cycloalkylene and arylene, wherein the arylene group is optionally substituted with one or more R¹¹;
R¹⁰ is selected from the group consisting of hydrogen, —C₁-C₆alkyl, —C₃-C₁₀cycloalkyl, haloalkyl, trihaloalkyl and aryl, wherein the aryl group is optionally substituted with one or more R¹¹;
L is a direct bond, —O— or —S—;
R¹¹ is halogen, hydroxy, —C₁-C₆alkyl, aryl, hetaryl, —C₃-C₁₀cycloalkyl, and —C₃-C₁₀hetcycloalkyl;
p is 0, 1, 2, 3 or 4; or
a pharmaceutically acceptable salt thereof.

Embodiment 2: A compound according to embodiment 1, wherein R¹ is hydrogen.

Embodiment 3: A compound according to embodiment 1 or 2, wherein each R² is hydrogen.

Embodiment 4: A compound according to any one of embodiments 1 through 3, wherein X is selected from the group consisting of —N(H)—, —O—, —S—, —S(O)— and —S(O₂)—.

Embodiment 5: A compound according to any one of embodiments 1 through 3, wherein X is —O—.

Embodiment 6: A compound according to any one of embodiments 1 through 3, wherein X is —S—.

Embodiment 7: A compound according to any one of embodiments 1 through 3, wherein X is —N(H)—.

Embodiment 8: A compound according to any one of embodiments 1 through 3, wherein X is —S(O)—.

Embodiment 9: A compound according to any one of embodiments 1 through 3, wherein X is —S(O₂)—.

Embodiment 10: A compound according to any one of embodiments 1 through 9, wherein V is =N—.

Embodiment 11: A compound according to embodiment 10, wherein U is =N—.

Embodiment 12: A compound according to embodiment 10, wherein W is =N—.

Embodiment 13: A compound according to any one of embodiments 10 through 12, wherein Z is =C(R⁷)—.

Embodiment 14: A compound according to embodiment 13, wherein R⁷ is selected from the group consisting of hydrogen, halogen, —C₁-C₆alkyl, trihalomethyl and —C₃-C₆cycloalkyl.

Embodiment 15: A compound according to embodiment 14, wherein R⁷ is halogen.

Embodiment 16: A compound according to embodiment 14, wherein R⁷ is chloro.

Embodiment 17: A compound according to embodiment 14, wherein R⁷ is trifluoromethyl.

Embodiment 18: A compound according to embodiment 14, wherein $R^7$ is hydrogen.

Embodiment 19: A compound according to embodiment 14, wherein $R^7$ is methyl.

Embodiment 20: A compound according to any one of embodiments 10 through 18, wherein Y is $=C(R^6)-$.

Embodiment 21: A compound according to embodiment 20, wherein $R^6$ is selected from the group consisting of hydrogen, halogen, $-C_1-C_6$alkyl, trihalomethyl and $-C_3-C_6$ cycloalkyl.

Embodiment 22: A compound according to embodiment 21, wherein $R^6$ is halogen.

Embodiment 23: A compound according to embodiment 21, wherein $R^6$ is chloro.

Embodiment 24: A compound according to embodiment 21, wherein $R^6$ is trifluoromethyl.

Embodiment 25: A compound according to embodiment 21, wherein $R^6$ is hydrogen.

Embodiment 26: A compound according to embodiment 21, wherein $R^6$ is methyl.

Embodiment 27: A compound according to embodiment 26, wherein $R^3$ is methyl.

Embodiment 28: A compound according to embodiment 10, wherein W is $=C(R^5)-$.

Embodiment 29: A compound according to embodiment 28, wherein $R^5$ is selected from the group consisting of halogen, $-C_1-C_6$alkyl, trihalomethyl and $-C_3-C_6$ cycloalkyl.

Embodiment 30: A compound according to embodiment 29, wherein $R^5$ is halogen.

Embodiment 31: A compound according to embodiment 29, wherein $R^5$ is chloro.

Embodiment 32: A compound according to embodiment 29, wherein $R^7$ is halogen.

Embodiment 33: A compound according to embodiment 29, wherein $R^7$ is chloro.

Embodiment 34: A compound according to embodiment 29, wherein $R^5$ is trifluoromethyl.

Embodiment 35: A compound according to embodiment 29, wherein $R^5$ is hydrogen.

Embodiment 36: A compound according to embodiment 29, wherein $R^5$ is methyl.

Embodiment 37: A compound according to embodiment 10, wherein U is $=C(R^3)-$.

Embodiment 38: A compound according to embodiment 37, wherein $R^3$ is selected from the group consisting of hydrogen, halogen, $-C_1-C_6$alkyl, trihalomethyl and $-C_3-C_6$ cycloalkyl.

Embodiment 39: A compound according to embodiment 38, wherein $R^3$ is halogen.

Embodiment 40: A compound according to embodiment 38, wherein $R^3$ is chloro.

Embodiment 41: A compound according to embodiment 38, wherein $R^3$ is trifluoromethyl.

Embodiment 42: A compound according to embodiment 38, wherein $R^3$ is hydrogen.

Embodiment 43: A compound according to embodiment 10, wherein Z is $=C(R^7)-$, Y is $=C(R^6)-$, W is $=C(R^5)-$ and U is $=C(R^3)-$.

Embodiment 44: A compound according to embodiment 43, wherein $R^3$, $R^5$, $R^6$ and $R^7$ are independently selected from the group consisting of hydrogen, halogen, $-C_1-C_6$alkyl, trihalomethyl and $-C_3-C_6$ cycloalkyl.

Embodiment 45: A compound according to embodiment 44, wherein $R^3$, $R^5$ and $R^6$ are hydrogen and $R^7$ is selected from the group consisting of hydrogen, halogen, $-C_1-C_6$alkyl, trihalomethyl and $-C_3-C_6$ cycloalkyl.

Embodiment 46: A compound according to embodiment 44, wherein $R^7$ is selected from the group consisting of chloro and trifluoromethyl.

Embodiment 47: A compound according to embodiment 1, wherein at least one of $R^3$, $R^4$, $R^5$, $R^6$ and $R^7$ is halogen.

Examples of compounds of Formula (I) of the present invention are shown in Table 1 and in the Examples section. The compounds specifically exemplified below were named based on their chemical structure using Autonom 2000 (Version 4.1, SP1, Elsevier MDL) plug-in for ISIS Draw.

TABLE 1

| Ex. | Structure | Name |
|---|---|---|
| 1 | 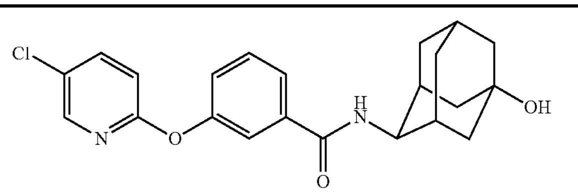 | 3-(5-Chloro-pyridin-2-yloxy)-N-(5-hydroxy-adamantan-2-yl)-benzamide |
| 2 | 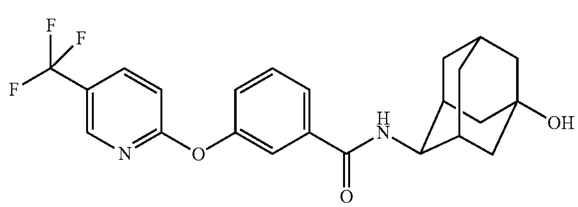 | N-(5-Hydroxy-adamantan-2-yl)-3-(5-trifluoromethyl-pyridin-2-yloxy)-benzamide |
| 3 | 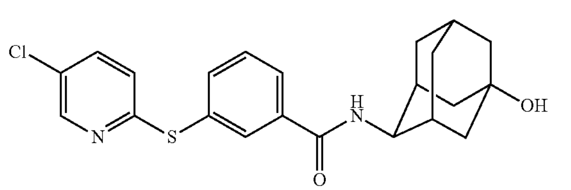 | 3-(5-Chloro-pyridin-2-ylsulfanyl)-N-(5-hydroxy-adamantan-2-yl)-benzamide |

TABLE 1-continued

| Ex. | Structure | Name |
|---|---|---|
| 4 | 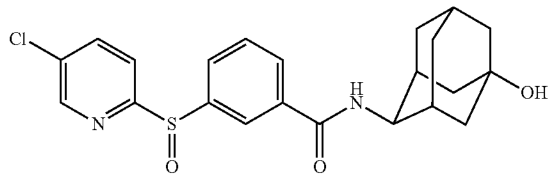 [SMILES: O=C(NC1C2CC3CC1CC(O)(C3)C2)c1cccc(S(=O)c2ccc(Cl)cn2)c1] | 3-(5-Chloro-pyridine-2-sulfinyl)-N-(5-hydroxy-adamantan-2-yl)-benzamide |
| 5 | 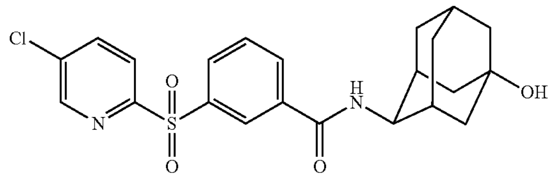 [SMILES: O=C(NC1C2CC3CC1CC(O)(C3)C2)c1cccc(S(=O)(=O)c2ccc(Cl)cn2)c1] | 3-(5-Chloro-pyridine-2-sulfonyl)-N-(5-hydroxy-adamantan-2-yl)-benzamide |
| 6 | 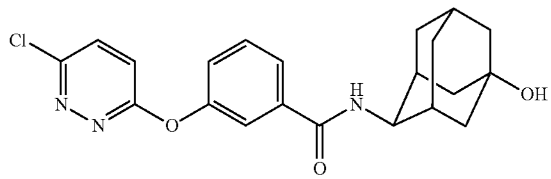 [SMILES: O=C(NC1C2CC3CC1CC(O)(C3)C2)c1cccc(Oc2ccc(Cl)nn2)c1] | 3-(6-Chloro-pyridazin-3-yloxy)-N-(5-hydroxy-adamantan-2-yl)-benzamide |
| 7 | 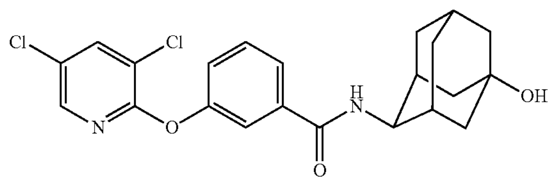 [SMILES: O=C(NC1C2CC3CC1CC(O)(C3)C2)c1cccc(Oc2ncc(Cl)cc2Cl)c1] | 3-(3,5-Dichloro-pyridin-2-yloxy)-N-(5-hydroxy-adamantan-2-yl)-benzamide |
| 8 | 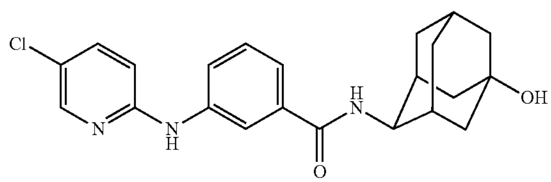 [SMILES: O=C(NC1C2CC3CC1CC(O)(C3)C2)c1cccc(Nc2ccc(Cl)cn2)c1] | 3-(5-Chloro-pyridin-2-ylamino)-N-(5-hydroxy-adamantan-2-yl)-benzamide |
| 9 | 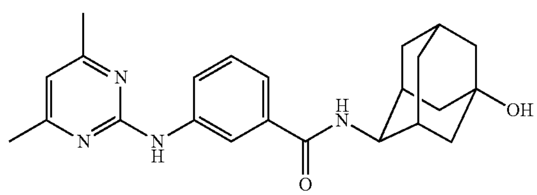 [SMILES: Cc1cc(C)nc(Nc2cccc(C(=O)NC3C4CC5CC3CC(O)(C5)C4)c2)n1] | 3-(4,6-Dimethyl-pyrimidin-2-ylamino)-N-(5-hydroxy-adamantan-2-yl)-benzamide |

Unless indicated otherwise, the structures of the Examples having vacant connectivity for heteroatoms, such as oxygen and nitrogen, are assumed to have a hydrogen atom attached thereto.

According to another embodiment of the present invention, methods for the preparation of hydroxyadamantylamine derivatives, or salts thereof, are described. These compounds may be useful as intermediates for the synthesis of chemical compounds, including the admantyl benzamide derivatives according to Embodiments 1 through 47 above. In one embodiment of the present invention, the hydroxyadamantylamine derivatives prepared according to methods of the present invention are E-isomer enriched. This E-isomer enrichment may be, for example, at least 60% E-isomer, typically at least 90% E-isomer, more typically at least 95% E-isomer, and often, at least 98% E-isomer. In one embodiment of the present invention, this E-enriched isomer is E-enriched 4-amino-admantan-1-ol.

A method according to the present invention may include a method for making E-enriched 4-amino-adamantan-1-ol, or a salt thereof. The method may include stirring a suspension of a mixture of E-4-amino-adamantan-1-ol and Z-4-amino-adamantan-1-ol in an alcoholic solvent wherein the suspension is at a temperature above 20° C. The E-4-amino-adamantan-1-ol and Z-4-amino-adamantan-1-ol compounds may be hydrochloric acid salts thereof. The alcoholic solvent may be, for example, methanol, ethanol, isopropanol or the like. In one embodiment, the alcohol may be methanol. The temperature of the suspension may be selected as a temperature at which the E-4-amino-adamantan-1-ol is less soluble in the alcoholic solvent than the Z-4-amino-adamantan-1-ol. For example, the temperature of the suspension may be about 60° C., may be above 50° C., may be above 50° C. and below the boiling point of the alcoholic solvent, or may be between 50° C. and 65° C. In another embodiment, the alcoholic solvent may be methanol and the temperature of the suspension may be about 60° C. or may be above 50° C. The suspension of the mixture of E- and Z-isomers in the alcoholic solvent may be stirred at the elevated temperature for a sufficient time to selectively dissolve the Z-isomer over the E-isomer. For example, this sufficient time may be from about 15 minutes to about 2 hours, typically about 30 minutes.

The method for making E-enriched 4-amino-adamantan-1-ol, or a salt thereof, may further include a step of separating the solids in the suspension aftering stirring the suspension at the elevated temperature for the sufficient time. For example, separating the solids may be accomplished by filtering the solids from the suspension aftering stirring the suspension at the elevated temperature for the sufficient time. In one embodiment of the present invention, the solids may be filtered without any substantial cooling of the suspension. The phrase "without any substantial cooling" may include some cooling of the suspension between the time period between when the heat is removed from the suspension to when the solids are filtered, however, no intentional delay to allow for cooling is intended.

The filtered solids may optionally be washed with an alcoholic solvent wherein the alcoholic solvent is at a temperature above 20° C. In an embodiment, the alcoholic solvent used to wash the filtered solids is at a temperature similar to, the same as, or above the temperature of the suspension when filtered. In another embodiment, the alcoholic solvent used to wash the filtered solids is at a temperature above 50° C. In any of the previous embodiments the alcoholic solvent used to wash the filtered solids may be the same alcoholic solvent used to selectively dissolve the E-4-amino-adamantan-1-ol and Z-4-amino-adamantan-1-ol. In an embodiment, the alcoholic solvent used to wash the filtered solids ismethanol. The filtered solids may then be dried to give the E-enriched 4-amino-adamantan-1-ol, or a salt thereof.

DEFINITIONS

The following definitions are meant to clarify, but not limit, the terms defined. If a particular term used herein is not specifically defined, such term should not be considered indefinite. Rather, terms are used within their ordinary meanings.

As used herein, the term "alkyl" refers to a straight or branched chain hydrocarbon having one to six carbon atoms, which may be optionally substituted as herein further described, with multiple degrees of substitution being allowed. Examples of "alkyl" as used herein include, but are not limited to, methyl, ethyl, propyl, isopropyl, isobutyl, n-butyl, tert-butyl, isopentyl, and n-pentyl.

As used herein, the term "alkylene" refers to a straight or branched chain divalent hydrocarbon radical having from one to six carbon atoms, which may be optionally substituted as herein further described, with multiple degrees of substitution being allowed. Examples of "alkylene" as used herein include, but are not limited to, methylene, ethylene, n-propylene, and n-butylene.

As used throughout this specification, the number of atoms, such as carbon atoms in an alkyl group, for example, will be represented by the phrase "$C_x$-$C_y$ alkyl," or "$C_{x\text{-}y}$ alkyl," which refer to an alkyl group, as herein defined, containing from x to y, inclusive, carbon atoms. Similar terminology will apply for other terms and ranges as well.

As used herein the term "halogen" or "halo" refers to fluorine, chlorine, bromine, or iodine.

As used herein the term "haloalkyl" refers to an alkyl group, as defined herein, that is substituted with at least one halogen. Examples of branched or straight chained "haloalkyl" groups as used herein include, but are not limited to, methyl, ethyl, propyl, isopropyl, n-butyl, and t-butyl substituted independently with one or more halogens, for example, fluoro, chloro, bromo, and iodo. The term "haloalkyl" should be interpreted to include groups such as —$CF_3$, —$CH_2$—$CF_3$, and —$CF_2Cl$.

As used herein, the term "alkoxy" or "alkyloxy" refers to the group $R^xO$—, where $R^x$ is alkyl.

As used herein, the term "alkyleneoxy" refers to the group —$R^xO$—, where $R^x$ is alkyl.

As used herein, the term "cycloalkyl" refers to an optionally substituted non-aromatic, three- to twelve-membered, cyclic hydrocarbon ring, optionally containing one or more degrees of unsaturation, which may be optionally substituted as herein further described, with multiple degrees of substitution being allowed. Exemplary "cycloalkyl" groups as used herein include, but are not limited to, cyclopropyl, cyclobutyl, cyclopentyl, cyclohexyl, and cycloheptyl, as well as rings containing one or more degrees of unsaturation but short of aromatic, such as cyclopropenyl, cyclobutenyl, cyclopentenyl, cyclohexenyl, and cycloheptenyl.

As used herein, the term "cycloalkylene" refers to a divalent, non-aromatic, three- to twelve membered, cyclic hydrocarbon ring, which may be optionally substituted as herein further described, with multiple degrees of substitution being allowed. Exemplary "cycloalkylene" groups include, but are not limited to, cyclopropylene, cyclobutylene, cyclopentylene, cyclohexylene, cycloheptylene, and substituted versions thereof. The term is intended to encompass divalent rings having different points of attachment as well as a common point of attachment, which connecting atom may also be referred to as "spiroatom."

As used herein, the terms "hetcyclic", "heterocyclic", "hetcycle", "heterocycle", "hetcyclyl", and "heterocyclyl" refers to an optionally substituted univalent non-aromatic mono- or polycyclic ring system, optionally containing one or more degrees of unsaturation and also containing one or more heteroatoms selected from the group consisting of nitrogen, oxygen, and sulfur, which may be optionally substituted, including oxidized, as herein further described, with multiple degrees of substitution being allowed. Typically, the ring is three to twelve-membered and is either fully saturated or has one or more degrees of unsaturation. Such rings may be optionally fused to one or more of another heterocyclic ring(s), cycloalkyl ring(s), aryl groups (as defined below) or heteroaryl groups (as defined below). Examples of "heterocyclic" groups as used herein include, but are not limited to, tetrahydrofuran, pyran, 1,4-dioxane, 1,3-dioxane, piperidine, pyrrolidine, morpholine, tetrahydrothiopyran, and tetrahydrothiophene.

As used herein, the term "aryl" refers to a benzene ring or to benzene ring fused to one to three benzene rings, optionally substituted and multiple degrees of substitution being allowed. Examples of aryl include, but are not limited to, phenyl, 2-naphthyl, 1-naphthyl, 1-anthracenyl, biphenyl, and the like.

As used herein, the term "arylene" refers to a divalent aromatic carbon containing ring or polycyclic fused ring system (up to three rings) where each ring contains between 3 to 7 atoms, which may be optionally substituted as herein further described, with multiple degrees of substitution being allowed. Examples of "arylene" include, but are not limited to, benzene-1,4-diyl, naphthalene-1,8-diyl.

As used herein, the term "heteroaryl" or "hetaryl" refers to a monocyclic five to seven membered aromatic ring, or to a fused bicyclic aromatic ring system comprising two of such aromatic rings, which may be optionally substituted as herein further described, with multiple degrees of substitution being allowed. These heteroaryl rings contain one or more nitrogen, sulfur, and/or oxygen atoms, where N-oxides, sulfur oxides, and dioxides are permissible heteroatom substitutions. Examples of "heteroaryl" groups as used herein include, but should not be limited to, furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzodioxolyl, benzothiophene, indole, indazole, benzimidizolyl, imidazopyridinyl, pyrazolopyridinyl, and pyrazolopyrimidinyl.

As used herein, the term "substituted" refers to substitution of one or more hydrogens of the designated moiety with the named substituent or substituents, multiple degrees of substitution being allowed unless otherwise stated, provided that the substitution results in a stable or chemically feasible compound. A stable compound or chemically feasible compound is one in which the chemical structure is not substantially altered when kept at a temperature from about −80° C. to about +40° C., in the absence of moisture or other chemically reactive conditions, for at least a week, or a compound which maintains its integrity long enough to be useful for therapeutic administration to a subject.

As used herein the terms "pharmaceutically acceptable carrier", "pharmaceutically acceptable diluent", and "pharmaceutically acceptable excipient" means the carrier, diluent or excipient must be compatible with the other ingredients of the formulation and not deleterious to the recipient thereof.

As used herein the term "therapeutically effective amount" as used herein means that amount of active compound or pharmaceutical agent that elicits the biological or medicinal response in a tissue, system, animal, human, or subject that is being sought by a researcher, veterinarian, medical doctor, patient or other clinician, which includes reduction or alleviation of the symptoms of the disease or condition being treated. When the active compound (i.e., active ingredient) is administered as the salt, references to the amount of active ingredient are to the free acid or free base form of the compound.

As used herein, "Subjects" include, for example, horses, cows, sheep, pigs, mice, dogs, cats, primates such as chimpanzees, gorillas, rhesus monkeys, and, humans. In an embodiment, a subject is a human.

In one embodiment the compound of the invention is an agent useful for the treatment, prevention and/or prophylaxis of any conditions, disorders and diseases wherein a modulation or an inhibition of the activity of 11βHSD1 is beneficial.

In one embodiment the compound of the invention is an agent useful for the treatment, prevention and/or prophylaxis of any conditions, disorders and diseases that are influenced by intracellular glucocorticoid levels.

In one embodiment the compound of the invention is an agent useful for the treatment, prevention and/or prophylaxis of conditions, disorders or diseases selected from the group consisting of the metabolic syndrome, insulin resistance, dyslipidemia, hypertension and obesity.

In one embodiment the compound of the invention is an agent useful for the treatment, prevention and/or prophylaxis of type 2 diabetes, impaired glucose tolerance (IGT), impaired fasting glucose (IFG).

In one embodiment the compound of the invention is an agent useful for the delaying or prevention of the progression from IGT into type 2 diabetes.

In one embodiment the compound of the invention is an agent useful for delaying or prevention of the progression of the metabolic syndrome into type 2 diabetes.

In one embodiment the compound of the invention is an agent useful for the treatment, prevention and/or prophylaxis of adverse effects of glucocorticoid receptor agonist treatment or therapy.

In one aspect, the invention relates to a pharmaceutical composition comprising, as an active ingredient, at least one compound according to the invention together with one or more pharmaceutically acceptable carriers or excipients.

In one aspect, the invention relates to a pharmaceutical composition which is for oral, nasal, buccal, transdermal, pulmonal or parenteral administration.

In one aspect, the invention relates to a pharmaceutical composition in unit dosage form, comprising from less than 2000 mg/day, less than 1000 mg/day, less than 500 mg/day or from 0.5 mg to 500 mg per day of the compound according to the invention.

In one aspect, the invention relates to a use of a compound according to the invention for the preparation of a pharmaceutical composition for the treatment, prevention and/or prophylaxis of any conditions, disorders and diseases wherein modulation or inhibition of the activity of 11βHSD1 is beneficial.

In one aspect, the invention relates to a use of a compound according to the invention for the preparation of a pharmaceutical composition for the treatment, prevention and/or prophylaxis of any conditions, disorders and diseases that are influenced by intracellular glucocorticoid levels.

In one aspect of the invention, the compounds according to the invention have an $IC_{50}$ value, as tested below, of less than 3000 nM, in a further aspect of the invention, some compounds may have $IC_{50}$ values below 500 nM, in yet a further aspect, some compounds may have $IC_{50}$ values below 300 nM, and, in yet a further aspect, below 200 nM.

Compounds of the present invention having asymmetric centers may occur as racemates, racemic mixtures, and as individual enantiomers or diastereoisomers, with all isomeric forms being included in the present invention as well as mixtures thereof.

Compounds of the present invention having cis-trans and/or E/Z isomerism may occur as either isomer or a mixture of both isomers.

The present invention also encompasses pharmaceutically acceptable salts of the present compounds. Such salts include pharmaceutically acceptable acid addition salts, pharmaceutically acceptable base addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxylnaphthoates, glycerophosphates, ketoglutarates and the like. Further examples of pharmaceutically acceptable inorganic or organic acid addition salts include the pharmaceutically acceptable salts listed in J. Pharm. Sci., 66, 2 (1977). Examples of metal salts include lithium, sodium, potassium, barium, calcium, magnesium, zinc, calcium salts and the like. Examples of amines and organic amines include ammonium, methylamine, dimethylamine, trimethylamine, ethylamine, diethylamine, propylamine, butylamine, tetramethylamine, ethanolamine, diethanolamine, triethanolamine, meglumine, ethylenediamine, choline, N,N'-dibenzylethylenediamine, N-benzylphenylethylamine, N-methyl-D-glucamine, guanidine and the like. Examples of cationic amino acids include lysine, arginine, histidine and the like.

The pharmaceutically acceptable salts may be prepared by reacting a compound of the present invention with a base such as sodium hydroxide, sodium methoxide, sodium hydride, potassium tert-butoxide, calcium hydroxide, magnesium hydroxide and the like, in solvents like ether, THF, methanol, tent-butanol, dioxane, isopropanol, ethanol etc. Mixtures of solvents may be used. Organic bases like lysine, arginine, diethanol-amine, choline, guandine and their derivatives etc. may also be used. Alternatively, acid addition salts wherever applicable are prepared by treatment with acids such as hydrochloric acid, hydrobromic acid, nitric acid, sulfuric acid, phosphoric acid, p-toluenesulphonic acid, methanesulfonic acid, acetic acid, citric acid, maleic acid salicylic acid, hydroxynaphthoic acid, ascorbic acid, palmitic acid, succinic acid, benzoic acid, benzenesulfonic acid, tartaric acid and the like in solvents like ethyl acetate, ether, alcohols, acetone, THF, dioxane etc. Mixture of solvents may also be used.

The compounds according to the invention alter, and more specifically, reduce the level of active intracellular glucocorticoid and are accordingly useful for the treatment, prevention and/or prophylaxis of disorders and diseases in which such a modulation or reduction is beneficial.

Accordingly, the present compounds may be applicable for the treatment, prevention and/or prophylaxis of metabolic syndrome, insulin resistance, dyslipidemia, hypertension, obesity, type 2 diabetes, impaired glucose tolerance (IGT), impaired fasting glucose (IFG), Latent Autoimmune Diabetes in the Adult (LADA), type 1 diabetes, diabetic late complications including cardiovascular diseases, cardiovascular disorders, disorders of lipid metabolism, neurodegenerative and psychiatric disorders, dysregulation of intraocular pressure including glaucoma, immune disorders, inappropriate immune responses, musculo-skeletal disorders, gastrointestinal disorders, polycystic ovarie syndrome (PCOS), reduced hair growth or other diseases, disorders or conditions that are influenced by intracellular glucocorticoid levels, adverse effects of increased blood levels of active endogenous or exogenous glucocorticoid, and any combination thereof, adverse effects of increased plasma levels of endogenous active glucocorticoid, Cushing's disease, Cushing's syndrome, adverse effects of glucocorticoid receptor agonist treatment of autoimmune diseases, adverse effects of glucocorticoid receptor agonist treatment of inflammatory diseases, adverse effects of glucocorticoid receptor agonist treatment of diseases with an inflammatory component, adverse effects of glucocorticoid receptor agonist treatment as a part of cancer chemotherapy, adverse effects of glucocorticoid receptor agonist treatment for surgical/post-surgical or other trauma, adverse effects of glucocorticoid receptor agonist therapy in the context of organ or tissue transplantation, or adverse effects of glucocorticoid receptor agonist treatment in other diseases, disorders or conditions where glucocorticoid receptor agonists provide clinically beneficial effects. Also the present compounds may be applicable for the treatment of visceral fat accumulation and insulin resistance in HAART (highly active antiretroviral treatment)-treated patients. Further, the present compounds may be applicable for the treatment of hydrocephalus as well as for the treatment or prevention of disorders related to the buildup of fluid within the ventricles of the brain.

More specifically the present compounds may be applicable for the treatment, prevention and/or prophylaxis of metabolic syndrome, type 2 diabetes, diabetes as a consequence of obesity, insulin resistance, hyperglycemia, prandial hyperglycemia, hyperinsulinemia, inappropriately low insulin secretion, impaired glucose tolerance (IGT), impaired fasting glucose (IFG), increased hepatic glucose production, type 1 diabetes, LADA, pediatric diabetes, dyslipidemia, diabetic dyslipidemia, hyperlipidemia, hypertriglyceridemia, hyperlipoproteinemia, hypercholesterolemia, decreased HDL cholesterol, impaired LDL/HDL ratio, other disorders of lipid metabolism, obesity, visceral obesity, obesity as a consequence of diabetes, increased food intake, hypertension, diabetic late complications, micro-/macroalbuminuria, nephropathy, retinopathy, neuropathy, diabetic ulcers, cardiovascular diseases, arteriosclerosis, atherosclerosis, coronary artery disease, cardiac hypertrophy, myocardial ischemia, heart insufficiency, congestive heart failure, stroke, myocardial infarction, arrythmia, decreased blood flow, erectile dysfunction (male or female), myopathy, loss of muscle tissue, muscle wasting, muscle catabolism, osteoporosis, decreased linear growth, neurodegenerative and psychiatric disorders, Alzheimer's disease, neuronal death, impaired cognitive function, depression, anxiety, eating disorders, appetite regulation, migraine, epilepsy, addiction to chemical substances, disorders of intraocular pressure, glaucoma, polycystic ovary syndrome (PCOS), inappropriate immune responses, inappropriate T helper-1/T helper-2 polarization, bacterial infections, mycobacterial infections, fungal infections, viral infections, parasitic infestations, suboptimal responses to immunizations, immune dysfunction, partial or complete baldness, or other diseases, disorders or conditions that are influenced by intracellular glucocorticoid levels and any combination thereof, adverse effects of glucocorticoid receptor agonist treatment of allergic-inflammatory diseases such as asthma and atopic dermatitis, adverse effects of glucocorticoid receptor agonist treatment of disorders of the respiratory system e.g. asthma, cystic fibrosis, emphysema, bronchitis, hypersensitivity, pneumonitis, eosinophilic pneumonias, pulmonary fibrosis, adverse effects of glucocorticoid receptor agonist treatment of inflammatory bowel disease such as Crohn's disease and ulcerative colitis; adverse effects of glucocorticoid receptor agonist treatment of disorders of the immune system, connective tissue and joints e.g. reactive arthritis, rheumatoid arthritis, Sjögren's syndrome, systemic lupus erythematosus, lupus nephritis, Henoch-Schönlein purpura, Wegener's granulomatosis, temporal arteritis, systemic sclerosis, vasculitis, sarcoidosis, dermatomyositis-polymyositis, pemphigus vulgaris; adverse effects of glucocorticoid receptor agonist treatment of endocrinological diseases such as hyperthyroidism, hypoaldosteronism, hypopituitarism; adverse effects of glucocorticoid receptor agonist treatment of hematological diseases e.g. hemolytic anemia, thrombocytopenia, paroxysmal nocturnal hemoglobinuria; adverse effects of glucocorticoid receptor agonist treatment of cancer such as spinal cord diseases, neoplastic compression of the spinal cord, brain tumours, acute lymphoblastic leukemia, Hodgkin's disease, chemotherapy-induced nausea, adverse effects of glucocorticoid receptor agonist treatment of diseases of muscle and at the neuro-muscular joint e.g. myasthenia gravis and heriditary myopathies (e.g. Duchenne muscular dystrophy), adverse effects of glucocorticoid receptor agonist treatment in the context of surgery & transplantation e.g. trauma, post-surgical stress, surgical stress, renal transplantation, liver transplantation, lung transplantation, pancreatic islet transplantation, blood stem cell transplantation, bone marrow transplantation, heart transplantation, adrenal gland transplantation, tracheal transplanttation, intestinal transplantation, corneal transplantation, skin grafting, keratoplasty, lens implantation and other procedures where immunosuppression with glucocorticoid receptor agonists is beneficial; adverse effects of glucocorticoid receptor agonist treatment of brain abscess, nausea/vomiting, infections, hypercalcemia, adrenal hyperplasia, autoimmune hepatitis, spinal cord diseases, saccular aneurysms or adverse effects to glucocorticoid receptor agonist treatment in other diseases, disorders and conditions where glucocorticoid receptor agonists provide clinically beneficial effects.

Accordingly, in a further aspect the invention relates to a compound according to the invention for use as a pharmaceutical composition.

The invention also relates to pharmaceutical compositions comprising, as an active ingredient, at least one compound according to the invention together with one or more pharmaceutically acceptable carriers or diluents.

The pharmaceutical composition may be in unit dosage form, comprising from about 0.05 mg/day to about 2000 mg/day, or from about 1 mg/day to about 500 mg/day of a compound according to the invention.

In another embodiment, the subject may be treated with a compound according to the invention for at least 1 week, for at least 2 weeks, for at least 4 weeks, for at least 2 months or for at least 4 months.

In yet another embodiment, the pharmaceutical composition is for oral, nasal, transdermal, pulmonal or parenteral administration.

Furthermore, the invention relates to the use of a compound according to the invention for the preparation of a pharmaceutical composition for the treatment, prevention and/or prophylaxis of disorders and diseases wherein a modulation or an inhibition of the activity of 11βHSD1 is beneficial.

The invention also relates to a method for the treatment, prevention and/or prophylaxis of disorders and diseases wherein a modulation or an inhibition of the activity of 11βHSD1 is beneficial, the method comprising administering to a subject in need thereof an effective amount of a compound according to the invention.

In one embodiment of the invention the present compounds are used for the preparation of a medicament for the treatment, prevention and/or prophylaxis of any diseases and conditions that are influenced by intracellular glucocorticoid levels as mentioned above.

Thus, in one embodiment of the invention the present compounds are used for the preparation of a medicament for the treatment, prevention and/or prophylaxis of conditions and disorders where a decreased level of active intracellular glucocorticoid is desirable, such as the conditions and diseases mentioned above.

In yet another embodiment of the invention the present compounds are used for the preparation of a medicament for the treatment, prevention and/or prophylaxis of the metabolic syndrome including insulin resistance, dyslipidemia, hypertension and obesity.

In yet another embodiment of the invention the present compounds are used for the preparation of a medicament for the treatment, prevention and/or prophylaxis of type 2 diabetes, impaired glucose tolerance (IGT), impaired fasting glucose (IFG).

In yet another embodiment of the invention the present compounds are used for the preparation of a pharmaceutical composition for the delaying or prevention of the progression from IGT to type 2 diabetes.

In yet another embodiment of the invention the present compounds are used for the preparation of a pharmaceutical composition for the delaying or prevention of the progression of the metabolic syndrome into type 2 diabetes.

In still another embodiment of the invention the present compounds are used for the preparation of a pharmaceutical composition for the treatment, prevention and/or prophylaxis of diabetic late complications including cardiovascular diseases; arteriosclerosis; atherosclerosis.

In a further embodiment of the invention the present compounds are used for the preparation of a pharmaceutical composition for the treatment, prevention and/or prophylaxis of neurodegenerative and psychiatric disorders.

In yet a further embodiment of the invention the present compounds are used for the preparation of a pharmaceutical composition for the treatment, prevention and/or prophylaxis of adverse effects of glucocorticoid receptor agonist treatment or therapy.

In another embodiment of the present invention, the route of administration may be any route which effectively transports a compound according to the invention to the appropriate or desired site of action, such as oral, nasal, buccal, transdermal, pulmonal, or parenteral.

In still a further aspect of the invention the present compounds are administered in combination with one or more further active substances in any suitable ratios. Such further active substances may e.g. be selected from antiobesity agents, antidiabetics, agents modifying the lipid metabolism, antihypertensive agents, glucocorticoid receptor agonists, agents for the treatment and/or prevention of complications resulting from or associated with diabetes and agents for the treatment and/or prevention of complications and disorders resulting from or associated with obesity.

Thus, in a further aspect of the invention the present compounds may be administered in combination with one or more antiobesity agents or appetite regulating agents.

Such agents may be selected from the group consisting of CART (cocaine amphetamine regulated transcript) agonists, NPY (neuropeptide Y) antagonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β3 agonists, MSH (melanocyte-stimulating hormone) agonists, MCH (melanocyte-concentrating hormone) antagonists, CCK (cholecystokinin) agonists, serotonin re-uptake inhibitors, serotonin and noradrenaline re-uptake inhibitors, mixed serotonin and noradrenergic compounds, 5HT (serotonin) agonists, bombesin agonists, galanin antagonists, growth hormone, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, PPAR (peroxisome proliferator-activated receptor) modulators, RXR (retinoid X receptor) modulators, TR β agonists, AGRP (Agouti related protein) inhibitors, H3 histamine antagonists, opioid antagonists (such as naltrexone), exendin-4, GLP-1 and ciliary neurotrophic factor.

In one embodiment of the invention the antiobesity agent is leptin; dexamphetamine or amphetamine; fenfluramine or dexfenfluramine; sibutramine; orlistat; mazindol or phentermine.

Suitable antidiabetic agents include insulin, insulin analogues and derivatives such as those disclosed in EP 792 290 (Novo Nordisk A/S), e.g. $N^{\epsilon B29}$-tetradecanoyl des (B30) human insulin, EP 214 826 and EP 705 275 (Novo Nordisk A/S), e.g. Asp$^{B28}$ human insulin, U.S. Pat. No. 5,504,188 (Eli Lilly), e.g. Lys$^{B28}$ Pro$^{B29}$ human insulin, EP 368 187 (Aventis), eg Lantus, which are all incorporated herein by reference, GLP-1 (glucagon like peptide-1) and GLP-1 derivatives such as those disclosed in WO 98/08871 to Novo Nordisk A/S, which is incorporated herein by reference as well as orally active hypoglycemic agents.

The orally active hypoglycemic agents may comprise sulphonylureas, biguanides, meglitinides, glucosidase inhibitors, glucagon antagonists such as those disclosed in WO 99/01423 to Novo Nordisk A/S and Agouron Pharmaceuticals, Inc., GLP-1 agonists, potassium channel openers such as those disclosed in WO 97/26265 and WO 99/03861 to Novo Nordisk A/S which are incorporated herein by reference, DPP-IV (dipeptidyl peptidase-IV) inhibitors, inhibitors of hepatic enzymes involved in stimulation of gluconeogenesis and/or glycogenolysis, glucose uptake modulators, compounds modifying the lipid metabolism such as antihyperlipidemic agents and antilipidemic agents as PPARα modulators, PPARδ modulators, cholesterol absorption inhibitors, HSL (hormone-sensitive lipase) inhibitors and HMG CoA inhibitors (statins), nicotinic acid, fibrates, anion exchangers, compounds lowering food intake, bile acid resins, RXR agonists and agents acting on the ATP-dependent potassium channel of the β-cells.

In one embodiment, the present compounds are administered in combination with insulin or an insulin analogue or derivative, such as $N^{\epsilon B29}$-tetradecanoyl des (B30) human insulin, Asp$^{B28}$ human insulin, Lys$^{B28}$ Pro$^{B29}$ human insulin, Lantus®, or a mix-preparation comprising one or more of these.

In a further embodiment the present compounds are administered in combination with a sulphonylurea e.g. tolbutamide, glibenclamide, glipizide or glicazide.

In another embodiment the present compounds are administered in combination with a biguanide e.g. metformin.

In yet another embodiment the present compounds are administered in combination with a meglitinide e.g. repaglinide or senaglinide.

In still another embodiment the present compounds are administered in combination with a thiazolidinedione e.g. troglitazone, ciglitazone, pioglitazone, rosiglitazone or compounds disclosed in WO 97/41097 such as 5-[[4-[3-Methyl-4-oxo-3,4-dihydro-2-quinazolinyl]methoxy]phenyl-methyl]thiazolidine-2,4-dione or a pharmaceutically acceptable salt thereof, such as the potassium salt.

In yet another embodiment the present compounds may be administered in combination with the insulin sensitizers disclosed in WO 99/19313 such as (–) 3-[4-[2-Phenoxazin-10-yl)ethoxy]phenyl]-2-ethoxypropanoic acid or a pharmaceutically acceptable salts thereof, such as the arginine salt.

In a further embodiment the present compounds are administered in combination with an α-glucosidase inhibitor e.g. miglitol or acarbose.

In another embodiment the present compounds are administered in combination with an agent acting on the ATP-dependent potassium channel of the β-cells e.g. tolbutamide, glibenclamide, glipizide, glicazide or repaglinide.

Furthermore, the present compounds may be administered in combination with nateglinide.

In still another embodiment the present compounds are administered in combination with an antihyperlipidemic agent or antilipidemic agent e.g. cholestyramine, colestipol, clofibrate, gemfibrozil, fenofibrate, bezafibrate, tesaglitazar, EML-4156, LY-818, MK-767, atorvastatin, fluvastatin, lovastatin, pravastatin, simvastatin, acipimox, probucol, ezetimibe or dextrothyroxine.

In a further embodiment the present compounds are administered in combination with more than one of the above-mentioned compounds e.g. in combination with a sulphonylurea and metformin, a sulphonylurea and acarbose, repaglinide and metformin, insulin and a sulphonylurea, insulin and metformin, insulin, insulin and lovastatin, etc.

Further, the present compounds may be administered in combination with one or more antihypertensive agents. Examples of antihypertensive agents are β-blockers such as alprenolol, atenolol, timolol, pindolol, propranolol, metoprolol, bisoprololfumerate, esmolol, acebutelol, metoprolol, acebutolol, betaxolol, celiprolol, nebivolol, tertatolol, oxprenolol, amusolalul, carvedilol, labetalol, β2-receptor blockers e.g. S-atenolol, OPC-1085, ACE (angiotensin converting enzyme) inhibitors such as quinapril, lisinopril, enalapril, captopril, benazepril, perindopril, trandolapril, fosinopril, ramipril, cilazapril, delapril, imidapril, moexipril, spirapril, temocapril, zofenopril, S-5590, fasidotril, Hoechst-Marion Roussel: 100240 (EP 00481522), omapatrilat, gemopatrilat and GW-660511, calcium channel blockers such as nifedipine, felodipine, nicardipine, isradipine, nimodipine, diltiazem, amlodipine, nitrendipine, verapamil, lacidipine, lercanidipine, aranidipine, cilnidipine, clevidipine, azelnidipine, barnidipine, efonodipine, iasidipine, iemildipine, iercanidipine, manidipine, nilvadipine, pranidipine, furnidipine, α-blockers such as doxazosin, urapidil, prazosin, terazosin, bunazosin and OPC-28326, diuretics such as thiazides/sulphonamides (e.g. bendroflumetazide, chlorothalidone, hydrochlorothiazide and clopamide), loop-diuretics (e.g. bumetanide, furosemide and torasemide) and potassium sparing diuretics (e.g. amiloride, spironolactone), endothelin ET-A antagonists such as ABT-546, ambrisetan, atrasentan, SB-234551, Cl-1034, S-0139 and YM-598, endothelin antagonists e.g. bosentan and J-104133, renin inhibitors such as aliskiren, vasopressin V1 antagonists e.g. OPC-21268, vasopressin V2 antagonists such as tolvaptan, SR-121463 and OPC-31260, B-type natriuretic peptide agonists e.g. Nesiritide, angiotensin II antagonists such as irbesartan, candesartancilexetil, losartan, valsartan, telmisartan, eprosartan, candesartan, CL-329167, eprosartan, iosartan, olmesartan, pratosartan, TA-606, and YM-358, 5-HT2 agonists e.g. fenoldopam and ketanserin, adenosine A1 antagonists such as naftopidil, N-0861 and FK-352, thromboxane A2 antagonists such as KT2-962, endopeptidase inhibitors e.g. ecadotril, nitric oxide agonists such as LP-805, dopamine D1 antagonists e.g. MYD-37, dopamine D2 agonists such as nolomirole, n-3 fatty acids e.g. omacor, prostacyclin agonists such as treprostinil, beraprost, PGE1 agonists e.g. ecraprost, Na+/K+ ATPase modulators e.g. PST-2238, Potassium channel activators e.g. KR-30450, vaccines such as PMD-3117, Indapamides, CGRP-unigene, guanylate cyclase stimulators, hydralazines, methyldopa, docarpamine, moxonidine, CoAprovel, MondoBiotech-811.

Further reference can be made to Remington: The Science and Practice of Pharmacy, 19$^{th}$ Edition, Gennaro, Ed., Mack Publishing Co., Easton, Pa., 1995.

Furthermore, the present compounds may be administered in combination with one or more glucocorticoid receptor agonists. Examples of such glucocorticoid receptor agonists are betametasone, dexamethasone, hydrocortisone, methylprednisolone, prednisolone, prednisone, beclomethasone, butixicort, clobetasol, flunisolide, flucatisone (and analogues), mometasone, triamcinolonacetonide, triamcinolonhexacetonide GW-685698, NXC-1015, NXC-1020, NXC-1021, NS-126, P-4112, P-4114, RU-24858 and T-25 series.

Pharmaceutical Compositions

The compounds of the present invention may be administered alone or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19$^{th}$ Edition, Gennaro, Ed., Mack Publishing Co., Easton, Pa., 1995.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route. It will be appreciated that the preferred route will depend on the general condition and age of the subject to be treated, the nature of the condition to be treated and the active ingredient chosen.

Pharmaceutical compositions for oral administration include solid dosage forms such as hard or soft capsules, tablets, troches, dragees, pills, lozenges, powders and granules. Where appropriate, they can be prepared with coatings such as enteric coatings or they can be formulated so as to provide controlled release of the active ingredient such as sustained or prolonged release according to methods well-known in the art.

Liquid dosage forms for oral administration include solutions, emulsions, suspensions, syrups and elixirs.

Pharmaceutical compositions for parenteral administration include sterile aqueous and non-aqueous injectable solutions, dispersions, suspensions or emulsions as well as sterile powders to be reconstituted in sterile injectable solutions or dispersions prior to use. Depot injectable formulations are also contemplated as being within the scope of the present invention.

Other suitable administration forms include suppositories, sprays, ointments, crèmes, gels, inhalants, dermal patches, implants etc.

A typical oral dosage is less than 100 mg/kg body weight per day, or from about 0.01 to about 50 mg/kg body weight per day, or from about 0.05 to about 10 mg/kg body weight per day administered in one or more dosages such as 1 to 3 dosages. The exact dosage will depend upon the frequency and mode of administration, the sex, age, weight and general condition of the subject treated, the nature and severity of the condition treated and any concomitant diseases to be treated and other factors evident to those skilled in the art.

The formulations may conveniently be presented in unit dosage form by methods known to those skilled in the art. A typical unit dosage form for oral administration one or more times per day such as 1 to 3 times per day may contain from less than 2000 mg, e.g. from 0.1 to 1000 mg, from 0.5 mg to 500 mg., from 1 mg to 200 mg, e.g. 100 mg.

For parenteral routes, such as intravenous, intrathecal, intramuscular and similar administration, typically doses are in the order of about half the dose employed for oral administration.

The compounds of this invention may be utilized as the free substance or as a pharmaceutically acceptable salt thereof. Examples are an acid addition salt of a compound having the utility of a free base and a base addition salt of a compound having the utility of a free acid. The term "pharmaceutically acceptable salts" refers to salts of the compounds for use according to the present invention which are generally prepared by reacting the free base with a suitable organic or inorganic acid or by reacting the acid with a suitable organic or inorganic base. When a compound for use according to the present invention, contains a free base such salts are prepared in a conventional manner by treating a solution or suspension of the compound with a chemical equivalent of a pharmaceutically acceptable acid. When a compounds for use according to the present invention, contains a free acid such salts are prepared in a conventional manner by treating a solution or suspension of the compound with a chemical equivalent of a pharmaceutically acceptable base. Physiologically acceptable salts of a compound with a hydroxy group include the anion of said compound in combination with a suitable cation such as sodium or ammonium ion. Other salts which are not pharmaceutically acceptable may be useful in the preparation of compounds for use according to the present invention and these form a further aspect of the present invention.

For parenteral administration, solutions of the present compounds in sterile aqueous solution, aqueous propylene glycol or sesame or peanut oil may be employed. Such aqueous solutions should be suitable buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Suitable pharmaceutical carriers include inert solid diluents or fillers, sterile aqueous solution and various organic solvents. Examples of suitable carriers are water, salt solutions, alcohols, polyethylene glycols, polyhydroxyethoxylated castor oil, peanut oil, olive oil, syrup, phosphorlipids, gelatine, lactose, terra alba, sucrose, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent may include any sustained release material known in the art, such as glyceryl monostearate or glyceryl distearate, alone or mixed with a wax. The formulations may also include wetting agents, emulsifying and suspending agents, preserving agents, sweetening agents or flavouring agents.

The pharmaceutical compositions formed by combining the compounds of the invention and the pharmaceutically acceptable carriers may be administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient, and which may include a suitable excipient. These formulations may be in the form of powder or granules, as a solution or suspension in an aqueous or non-aqueous liquid, or as an oil-in-water or water-in-oil liquid emulsion.

Compositions intended for oral use may be prepared according to any known method, and such compositions may contain one or more agents selected from the group consisting of sweetening agents, flavoring agents, coloring agents, and preserving agents in order to provide pharmaceutically elegant and palatable preparations. Tablets may contain the active ingredient in admixture with non-toxic pharmaceutically-acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch or alginic acid; binding agents, for example, starch, gelatine or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,356,108; 4,166,452; and 4,265,874, to form osmotic therapeutic tablets for controlled release.

Formulations for oral use may also be presented as hard gelatine capsules where the active ingredient is mixed with an inert solid diluent, for example, calcium carbonate, calcium phosphate or kaolin, or a soft gelatine capsule wherein the active ingredient is mixed with water or an oil medium, for example peanut oil, liquid paraffin, or olive oil.

Aqueous suspensions may contain the active compounds in admixture with excipients suitable for the manufacture of aqueous suspensions. Such excipients are suspending agents, for example sodium carboxymethylcellulose, methylcellulose, hydroxy-propylmethylcellulose, sodium alginate, polyvinylpyrrolidone, gum tragacanth and gum acacia; dispersing or wetting agents may be a naturally-occurring phosphatide such as lecithin, or condensation products of an alkylene oxide with fatty acids, for example poly-oxyethylene stearate, or condensation products of ethylene oxide with long chain aliphatic alcohols, for example, heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more coloring agents, one or more flavouring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as a liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example, sweetening, flavoring, and coloring agents may also be present.

The pharmaceutical compositions comprising a compound for use according to the present invention may also be in the form of oil-in-water emulsions. The oily phase may be a vegetable oil, for example, olive oil or arachis oil, or a mineral oil, for example a liquid paraffin, or a mixture thereof. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, preservative and flavoring and coloring agent. The pharmaceutical compositions may be in the form of a sterile injectable aqueous or oleaginous suspension. This suspension may be formulated according to the known methods using suitable dispersing or wetting agents and suspending agents described above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution, and isotonic sodium chloride solution. In addition, sterile, fixed oils are conveniently employed as solvent or suspending medium. For this purpose, any bland fixed oil may be employed using synthetic mono- or diglycerides. In addition, fatty acids such as oleic acid find use in the preparation of injectables.

The compositions may also be in the form of suppositories for rectal administration of the compounds of the present invention. These compositions can be prepared by mixing the drug with a suitable non-irritating excipient which is solid at ordinary temperatures but liquid at the rectal temperature and will thus melt in the rectum to release the drug. Such materials include cocoa butter and polyethylene glycols, for example.

For topical use, creams, ointments, jellies, solutions of suspensions, etc., containing the compounds of the present invention are contemplated. For the purpose of this application, topical applications shall include mouth washes and gargles.

Thus, in a further embodiment, there is provided a pharmaceutical composition comprising a compound for use according to the present invention, or a pharmaceutically acceptable salt thereof, and one or more pharmaceutically acceptable carriers, excipients, or diluents.

If a solid carrier is used for oral administration, the preparation may be tableted, placed in a hard gelatine capsule in powder or pellet form or it can be in the form of a troche or lozenge. The amount of solid carrier may vary but will usually be from 25 mg to 1 g. If a liquid carrier is used, the preparation may be in the form of a syrup, emulsion, soft gelatine capsule or sterile injectable liquid such as an aqueous or non-aqueous liquid suspension or solution.

The compounds of the invention may be administered to a patient which is a mammal, especially a human in need thereof. Such mammals include also animals, both domestic animals, e.g. household pets, and non-domestic animals such as wildlife.

The features disclosed in the foregoing description may, both separately and in any combination thereof, be material for realizing the invention in diverse forms thereof.

Any combination of the above-described elements in all possible variations thereof is encompassed by the invention unless otherwise indicated herein or otherwise clearly contradicted by context.

The terms "a" and "an" and "the" and similar referents as used in the context of describing the invention are to be construed to cover both the singular and the plural, unless otherwise indicated herein or clearly contradicted by context.

All methods described herein can be performed in any suitable order unless otherwise indicated herein or otherwise clearly contradicted by context.

The present invention is further illustrated in the following representative examples which are, however, not intended to limit the scope of the invention in any way. The compounds of Formula (I) may be prepared according to the following Examples. In these Examples, it is also possible to make use of variants that are themselves known to those of ordinary skill in this art, but are not mentioned in greater detail.

EXAMPLES

LC-MS data was obtained using gradient elution on a parallel MUX™ system, running four Waters 1525 binary HPLC pumps, equipped with a Mux-UV 2488 multichannel UV-Vis detector (recording at 215 and 254 nM) and a Leap Technologies HTS PAL Auto sampler using a Waters Xterra MS C18 4.6×50 mm column. A three minute gradient was run from 25% B (97.5% acetonitrile, 2.5% water, 0.05% TFA) and 75% A (97.5% water, 2.5% acetonitrile, 0.05% TFA) to 100% B. The system is interfaced with a Waters Micromass ZQ mass spectrometer using electrospray ionization. All MS data was obtained in the positive mode unless otherwise noted. 1H NMR data was obtained on a Varian 400 MHz spectrometer. Abbreviations that may be used in the Examples are as follows:
BINAP=2,2'-bis(diphenylphosphino)-1,1'-binaphthyl
DMF=N,N-dimethylformamide
ELISA=enzyme-linked immunosorbent assay
g=gram
h=hour
HBTU=O-benzotriazol-1-yl-N,N,N',N'-tetramethyluronium hexafluorophosphate
M=molar
m/z=mass to charge ratio
mg=milligram
min=minute
mL=milliliter
μL=microliter
mM=millimolar
mmol=millimole
mol=mole
MS=mass spectrometry
N=normal
NaOH=sodium hydroxide
NMR=nuclear magnetic resonance spectroscopy
rt=room temperature
THF=tetrahydrofuran Preparation A: E-enriched 4-amino-admantan-1-ol

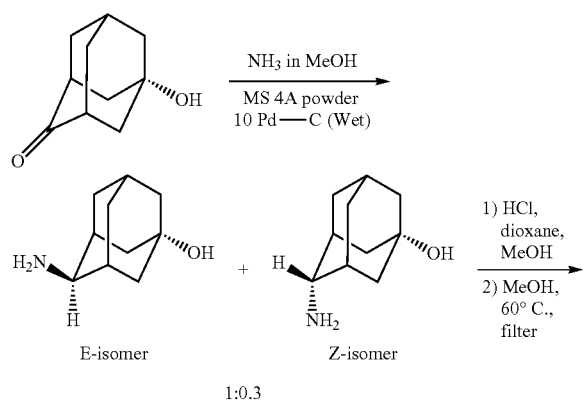

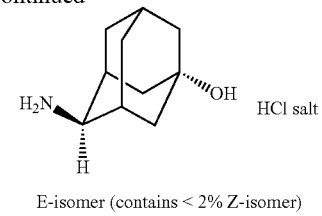

E-isomer (contains < 2% Z-isomer)

5-Hydroxy-adamantan-2-one (Lachema, 673 g, 4 moles) was dissolved in 7 M ammonia in methanol (2.5 L) and molecular sieves 4A powder (175 g) was added. The suspension was stirred for 3 h at room temperature. The contents were then transferred to a Parr hydrogenation vessel and 10% palladium on charcoal (40 g) was added. The contents were subjected to hydrogen at 100 PSI. When the reaction was complete the contents were filtered over a 6-inch thick pad of Celite and concentrated to half-volume. The contents were cooled to room temperature in a water-bath. Then a study stream of 4N HCl in dioxane (1.1 L) was added carefully using an addition funnel with vigorous stirring. The reaction mixture was stirred for 30 min at room temperature. The solids were filtered and were transferred to a 5-L round bottom flask. Methanol (750 mL) was added and the contents were heated to 60° C. with stirring for 30 minutes. The solids were filtered, air-dried and dried under reduced pressure to obtain E-4-amino-adamantan-1-ol (450 g, 55%) which contains <2% of Z-isomer as indicated by $^1$H NMR analysis. $^1$H NMR (400 MHz, D$_2$O): δ 1.40-1.50 (2 br s, 2H), 1.60-1.70 (m, 8H), 2.00-2.10 (2 br s, 3H), 3.24 (m, 0.02 H, Z-isomer), 3.34 (m, 0.98 H, E-isomer). NH$_3$ and OH are not detected as these protons are exchangeable with deuterium.

Example 1

3-(5-Chloro-pyridin-2-yloxy)-N-[(E)-5-hydroxy-adamantan-2-yl]-benzamide

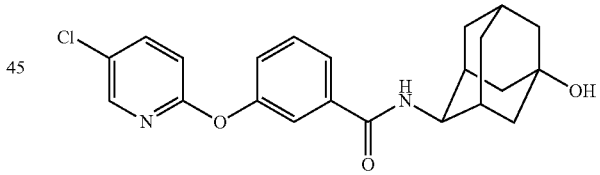

To a dimethylformamide (100 mL) solution of 3-hydroxy-benzoic acid methyl ester (3.5 g, 23 mmol) was added potassium t-butoxide (3.2 g, 28 mmol). Upon stirring the reaction at room temperature for 15 min, 2-bromo-5-chloro-pyridine was added. The reaction was heated to 130° C. for 15 h. Crude reaction mass was added to water, and extracted with diethyl ether to remove unhydrolyzed methyl ester, 3-(5-chloro-pyridin-2-yloxy)-benzoic acid methyl ester (2.5 g). The aqueous layer was acidified to pH 4.0 and product was extracted with ethyl acetate to give 3-(5-chloro-pyridin-2-yloxy)-benzoic acid (2.0 g). Saponification of methyl ester (2.5 g, 9.4 mmol) using NaOH (1.0 g, 25 mmol) in methanol:THF:water (1:1:1, 60 mL) furnished additional 2.0 g of 3-(5-chloro-pyridin-2-yloxy)-benzoic acid.

A mixture of 3-(5-chloro-pyridin-2-yloxy)-benzoic acid (249 mg, 1.0 mmol), 3:1 mixture of E- and Z-4-amino-adamantan-1-ol (183 mg, 1.1 mmol), HBTU (417 mg, 1.1 mmol), diisopropylethyl amine (0.35 ml, 2.0 mmol) in DMF (3.0 mL) was stirred at room temperature for 1 h. Water was added and product was extracted with ethyl acetate. Crude product was purified by flash column chromatography using 20% hexanes in ethyl acetate using a prepacked silica column to obtain 3-(5-chloro-pyridin-2-yloxy)-N-[(E)-5-hydroxy-adamantan-2-yl]-benzamide (150 mg).

LC-MS (m/z): 399.96 (M+1)$^+$; $^1$H NMR (400 MHz, CDCl$_3$): δ 8.11 (d, 1H), 7.68 (dd, 1H), 7.53-7.61 (m, 2H), 7.48 (t, 1H) 7.24-7.31 (m, 1H), 6.94 (d, 1H), 6.30 (br d, 1H), 4.18-4.24 (m, 1H), 2.17-2.28 (m, 3H), 1.89-1.98 (m, 2H), 1.72-1.84 (m, 6H), 1.54-1.67 (m, 4H) ppm.

Example 2

N-[(E)-5-Hydroxy-adamantan-2-yl]-3-(5-trifluoromethyl-pyridin-2-yloxy)-benzamide

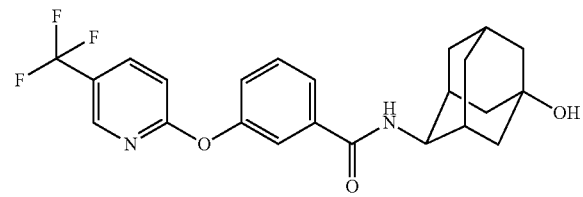

To a dimethylformamide (1.0 mL) solution of 3-hydroxy-benzoic acid methyl ester (183 mg, 1.2 mmol) was added potassium t-butoxide (147 mg, 1.2 mmol). Upon stirring the reaction at room temperature for 15 min, 2-bromo-5-trifluoromethyl-pyridine (300 mg, 1.32 mmol) was added. The reaction was stirred at room temperature for 15 h. Crude reaction mass was added to water, aqueous layer was acidified to pH 4.0 and product was extracted with ethyl acetate to give 3-(5-trifluoromethyl-pyridin-2-yloxy)-benzoic acid methyl ester (285 mg).

A mixture of 3-(5-trifluoromethyl-pyridin-2-yloxy)-benzoic acid methyl ester (285 g, 0.95 mmol) and NaOH (200 mg, 4 mmol) in methanol:THF:water (1:1:1, 3 mL) was stirred at room temperature for 8 h. Solvents were evaporated. Crude mass was taken in water (20 mL), acidified to pH 4.0 and extracted with ethyl acetate to obtain 3-(5-trifluoromethyl-pyridin-2-yloxy)-benzoic acid was prepared (215 mg).

A mixture of 3-(5-trifluoromethyl-pyridin-2-yloxy)-benzoic acid (100 mg, 0.35 mmol), 3:1 mixture of E- and Z-4-amino-adamantan-1-ol (78 mg, 0.385 mmol), HBTU (146 mg, 0.385 mmol), diisopropylethyl amine (0.20 ml, 0.8 mmol) in DMF (1.0 mL) was stirred at room temperature for 1 h. Water was added and product was extracted with ethyl acetate. Crude product was purified by flash column chromatography using 20% hexanes in ethyl acetate using a prepacked silica column to obtain N-[(E)-5-hydroxy-adamantan-2-yl]-3-(5-trifluoromethyl-pyridin-2-yloxy)-benzamide (75 mg).

LC-MS (m/z): 434.0 (M+1)$^+$; $^1$H NMR (400 MHz, CDCl$_3$): δ 8.43 (s, 1H) 7.94 (dd, 1H), 7.57-7.66 (m, 2H), 7.51 (t, 1H), 7.31 (m, 1H), 7.08 (d, 1H), 6.31 (d, 1H), 4.18-4.26 (m, 1H), 2.17-2.30 (m, 3H), 1.91-1.99 (m, 2H), 1.74-1.85 (m, 6H), 1.55-1.65 (m, 4H) ppm.

Example 3

3-(5-Chloro-pyridin-2-ylsulfanyl)-N-[(E)-5-hydroxy-adamantan-2-yl]-benzamide

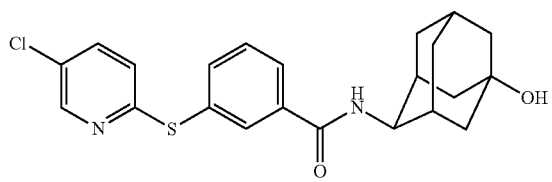 [SMILES: O=C(NC1C2CC3CC1CC(O)(C3)C2)c1cccc(Oc2ccc(Cl)cn2)c1]

To a dimethylformamide (7.0 mL) solution of 3-mercapto-benzoic acid methyl ester (600 mg, 3.5 mmol) was added potassium t-butoxide (500 mg, 4.0 mmol). Upon stirring the reaction at room temperature for 15 min, 2-bromo-5-chloro-pyridine (700 mg, 3.5 mmol) was added. The reaction was stirred at room temperature for 15 h. Crude reaction mass was added to water, aqueous layer was acidified to pH 4.0 and product was extracted with ethyl acetate to give 3-(5-chloro-pyridin-2-ylsulfanyl)-benzoic acid methyl ester (780 mg).

A solution of 3-(5-chloro-pyridin-2-ylsulfanyl)-benzoic acid methyl ester (780 g, 2.8 mmol) and NaOH (500 mg, 12 mmol) in methanol:THF:water (1:1:1, 6 mL) was stirred at room temperature for 8 h. Solvents were evaporated. Crude mass was taken in water (40 mL), acidified to pH 4.0 and extracted with ethyl acetate. Evaporation of ethyl acetate provided 3-(5-chloro-pyridin-2-ylsulfanyl)-benzoic acid (580 mg).

A mixture of 3-(5-chloro-pyridin-2-ylsulfanyl)-benzoic acid (130 mg, 0.48 mmol), (E)-4-amino-adamantan-1-ol.hydrochloride (109 mg, 0.53 mmol), HBTU (200 mg, 0.53 mmol), diisopropylethyl amine (0.20 ml, 1.0 mmol) in DMF (1.0 mL) was stirred at room temperature for 1 h. Water was added and product was extracted with ethyl acetate. Crude product was purified by flash column chromatography using 20% hexanes in ethyl acetate using a prepacked silica column to obtain 3-(5-chloro-pyridin-2-ylsulfanyl)-N-[(E)-5-hydroxy-adamantan-2-yl]-benzamide (100 mg).

LC-MS (m/z): 415.86 (M+1)$^+$; $^1$H NMR (400 MHz, CDCl$_3$): δ 8.39 (d, 1H), 7.03-8.02 (m, 1H), 7.82 (d, 1H), 7.70 (d, 1H), 7.46-7.54 (m, 2H), 6.95 (d, 1H), 6.29 (d, 1H), 4.18-4.25 (m, 1H), 2.17-2.28 (m, 3H), 1.92-1.99 (m, 2H), 1.73-1.84 (m, 6H), 1.60 (m, 4H) ppm.

Example 4

3-(5-Chloro-pyridine-2-sulfinyl)-N-[(E)-5-hydroxy-adamantan-2-yl]-benzamide

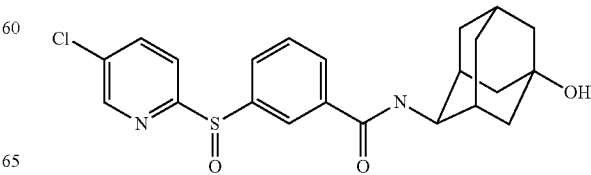

A mixture of 3-(5-chloro-pyridin-2-ylsulfanyl)-N-[(E)-5-hydroxy-adamantan-2-yl]-benzamide (40 mg, 0.09 mmol), acetic acid (0.5 mL) and 50% hydrogen peroxide in acetic acid (0.5 mL) was stirred at room temperature for 2 h. Crude reaction mass was added to saturated sodium bicarbonate solution and product extracted with ethyl acetate. Crude product was filtered through a bed of silica gel using hexane:ethyl acetate. Evaporation of solvents yielded 3-(5-chloro-pyridine-2-sulfinyl)-N-[(E)-5-hydroxy-adamantan-2-yl]-benzamide (10 mg)

LC-MS (m/z): 431.9 (M+1)$^+$; $^1$H NMR (400 MHz, CD$_3$OD): δ 8.59 (d, 1H), 8.18 (m, 1H), 8.07-8.11 (m, 1H), 8.00-8.05 (m, 1H), 7.92 (m, 2H), 7.59-7.66 (m, 2H), 4.07 (br t., 1H), 2.24 (br s., 2H), 2.11-2.16 (m, 1H), 2.00 (d, 2H), 1.88 (br m., 2H), 1.76-1.82 (m, 5H), 1.54 (br d., 2H) ppm.

Example 5

3-(5-Chloro-pyridine-2-sulfonyl)-N-[(E)-5-hydroxy-adamantan-2-yl]-benzamide

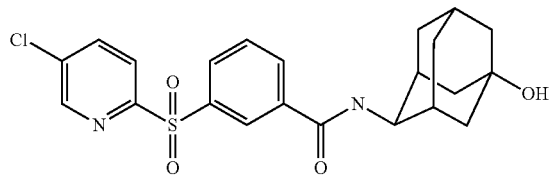 [SMILES: O=C(NC1C2CC3CC1CC(O)(C3)C2)c1cccc(S(=O)(=O)c2ccc(Cl)cn2)c1]

A solution of 3-(5-chloro-pyridin-2-ylsulfanyl)-N-(5-hydroxy-adamantan-2-yl)-benzamide (60 mg, 0.14 mmol), acetic acid (0.5 mL) and 30% peracetic acid solution in acetic acid (1.0 mL) was stirred at room temperature for 8 h. Crude reaction mass was added to saturated sodium bicarbonate solution and product extracted with ethyl acetate. Crude product was filtered through a bed of silica gel using hexane:ethyl acetate. Evaporation of solvents provided 3-(5-chloro-pyridine-2-sulfonyl)-N-[(E)-5-hydroxy-adamantan-2-yl]-benzamide (20 mg).

LC-MS (m/z): 447.87 (M+1)$^+$; $^1$H NMR (400 MHz, CD$_3$OD): δ 8.65 (d, 1H), 8.39 (m, 1H), 8.23-8.27 (m, 1H), 8.08-8.18 (m, 3H), 7.70 (t, 1H), 4.08 (m, 1H), 2.24 (br s, 2H), 2.13 (br s, 1H), 1.97-2.05 (m, 3H), 1.86-1.92 (m, 2H), 1.75-1.82 (m, 4H), 1.52 (d, 2H) ppm (amide NH not detected).

Example 6

3-(6-Chloro-pyridazin-3-yloxy)-N-[(E)-5-hydroxy-adamantan-2-yl]-benzamide

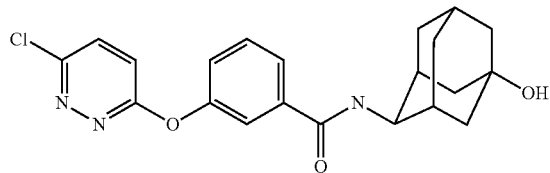 [SMILES: O=C(NC1C2CC3CC1CC(O)(C3)C2)c1cccc(Oc2ccc(Cl)nn2)c1]

To a dimethylformamide (8.0 mL) solution of 3-hydroxy-benzoic acid methyl ester (928 mg, 6.1 mmol) was added potassium t-butoxide (750 mg, 6.7 mmol). Upon stirring the reaction at room temperature for 15 min, 3,6-dichloro-pyridazine (1.0 g, 6.7 mmol) was added. The reaction was stirred at room temperature for 15 h. Crude reaction mass was added to water, aqueous layer was acidified to pH 4.0 and product was extracted with ethyl acetate to give 3-(6-chloro-pyridazin-3-yloxy)-benzoic acid methyl ester (950 mg).

A mixture of 3-(6-chloro-pyridazin-3-yloxy)-benzoic acid methyl ester (950 g, 3.6 mmol) and NaOH (700 mg, 16 mmol) in methanol:THF:water (1:1:1, 6 mL) was stirred at room temperature for 8 h, solvents were evaporated. Crude mass was taken in water (40 mL), acidified to pH 4.0 and extracted with ethyl acetate. Evaporation of ethyl acetate furnished 3-(6-chloro-pyridazin-3-yloxy)-benzoic acid (580 mg).

A mixture of 3-(6-chloro-pyridazin-3-yloxy)-benzoic acid (140 mg, 0.56 mmol), (E)-4-amino-adamantan-1-ol.hydrochloride (125 mg, 0.61 mmol), HBTU (230 mg, 0.61 mmol), diisopropylethylamine (0.30 ml, 1.2 mmol) in DMF (1.0 mL) was stirred at room temperature for 1 h. Water was added and product was extracted with ethyl acetate. Crude product was purified by flash column chromatography using 20% hexanes in ethyl acetate using a prepacked silica column to obtain 3-(6-chloro-pyridazin-3-yloxy)-N-[(E)-5-hydroxy-adamantan-2-yl]-benzamide (20 mg).

LC-MS (m/z): 400.86 (M+1)$^+$; $^1$H NMR (400 MHz, CD$_3$OD): δ 7.71-7.81 (m, 1H), 7.65 (m, 1H), 7.46-7.61 (m, 2H), 7.24-7.42 (m, 2H), 4.07 (br t, 1H), 2.24 (br s, 2H), 2.09-2.16 (m, 1H), 1.99 (d, 3H), 1.87 (br m, 2H), 1.73-1.82 (m, 5H), 1.53 (br m, 2H) ppm (amide NH not detected).

Example 7

3-(3,5-Dichloro-pyridin-2-yloxy)-N-[(E)-5-hydroxy-adamantan-2-yl]-benzamide

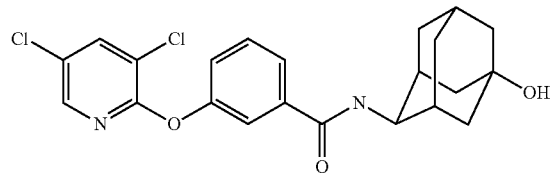 [SMILES: O=C(NC1C2CC3CC1CC(O)(C3)C2)c1cccc(Oc2ncc(Cl)cc2Cl)c1]

To a dimethylformamide (5.0 mL) solution of 3-hydroxy-benzoic acid methyl ester (760 mg, 5.0 mmol) was added potassium t-butoxide (613 mg, 5.48 mmol). Upon stirring the reaction at room temperature for 15 min, 2,3,5-trichloro-pyridine (1.0 g, 5.48 mmol) was added. The reaction was stirred at room temperature for 15 h. Crude reaction mass was added to water, aqueous layer was acidified to pH 4.0 and product was extracted with ethyl acetate to give 3-(3,5-cichloro-pyridin-2-yloxy)-benzoic acid methyl ester (1100 mg).

A mixture of 3-(3,5-dichloro-pyridin-2-yloxy)-benzoic acid methyl ester (1100 mg, 4.0 mmol) and NaOH (700 mg, 16 mmol) in methanol:THF:water (1:1:1, 6 mL) was stirred at room temperature for 8 h. Solvents were evaporated. Crude mass was taken in water (40 mL), acidified to pH 4.0 and extracted with ethyl acetate. Evaporation of ethyl acetate yielded 3-(3,5-dichloro-pyridin-2-yloxy)-benzoic acid (908 mg).

A solution of 3-(5-chloro-pyridin-2-ylsulfanyl)-benzoic acid (100 mg, 0.35 mmol), 3:1 mixture of E- and Z-4-amino-adamantan-1-ol (65 mg, 0.38 mmol), HBTU (144 mg, 0.38 mmol), diisopropylethyl amine (0.12 ml, 0.7 mmol) in DMF (1.0 mL) was stirred at room temperature for 1 h. Water was added and product was extracted with ethyl acetate. Crude product was purified by flash column chromatography using 20% hexanes in ethyl acetate using a prepacked silica column to obtain 3-(3,5-dichloro-pyridin-2-yloxy)-N-[(E)-5-hydroxy-adamantan-2-yl]-benzamide (50 mg).

LC-MS (m/z): 433.93 (M+1)+; 1H NMR (400 MHz, CD3OD): δ 8.04 (d, 1H), 7.99 (d, 1H), 7.69 (d, 1H), 7.59 (d, 1H), 7.51 (t, 1H), 7.30 (dd, 1H), 4.06 (br m., 1H), 2.23 (br s., 2H), 2.11 (br m., 1H), 1.99 (br d, 2H), 1.84-1.92 (m, 2H), 1.74-1.81 (m, 4H), 1.50 (br d, 2H) ppm (amide NH and alcohol OH not detected).

Example 8

3-(5-Chloro-pyridin-2-ylamino)-N-[(E)-5-hydroxy-adamantan-2-yl]-benzamide

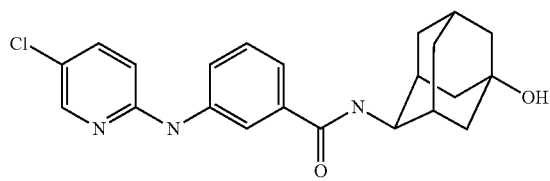 [SMILES: O=C(NC1C2CC3CC1CC(O)(C3)C2)c1cccc(Nc2ccc(Cl)cn2)c1]

To a toluene (10.0 mL) solution of 3-amino-benzoic acid methyl ester (330 mg, 2.2 mmol) was added palladium acetate (200 μL of 0.001 mmol stock solution), BINAP (200 μL of 0.001 mmol stock colution), sodium t-butoxide (2.2 mmol) and 2,5-dichloro-pyridine (296 mg, 2.0 mmol). The reaction mixture was refluxed for 10 h. Collected crude reaction mass was added to water, extracted with ethyl acetate. Solvent was evaporated and the crude mass was purified by flash column chromatography using 20% ethyl acetate in hexanes on a prepacked silica column to give 3-(5-chloro-pyridin-2-ylamino)-benzoic acid methyl ester (315 mg).

A mixture of 3-(5-chloro-pyridin-2-ylamino)-benzoic acid methyl ester (315 mg, 1.2 mmol) and NaOH (200 mg, 5.0 mmol) in methanol:THF:water (1:1:1, 3 mL) was stirred at room temperature for 8 h. Solvents were evaporated. Crude mass was taken in water (40 mL), acidified to pH 4.0 and extracted with ethyl acetate to obtain 3-(5-chloro-pyridin-2-ylamino)-benzoic acid (238 mg).

A solution of 3-(5-chloro-pyridin-2-ylamino)-benzoic acid (120 mg, 0.50 mmol), 3:1 mixture of E- and Z-4-amino-adamantan-1-ol (100 mg, 0.55 mmol), HBTU (200 mg, 0.55 mmol), diisopropylethyl amine (0.17 ml, 1.0 mmol) in DMF (2.0 mL) was stirred at room temperature for 1 h. Water was added and product was extracted with ethyl acetate. Crude product was purified by flash column chromatography using 20% hexanes in ethyl acetate using a prepacked silica column to obtain 3-(5-chloro-pyridin-2-ylamino)-N-[(E)-5-hydroxy-adamantan-2-yl]-benzamide (90 mg).

LC-MS (m/z): 398.99 (M+1)+; 1H NMR (400 MHz, CD3OD): δ 8.00-8.09 (m, 2H), 7.67 (m, 1H), 7.55 (dd, 1H), 7.32-7.38 (m, 2H), 6.82 (d, 1H), 4.05-4.10 (m, 1H), 2.24 (br s., 2H), 2.13-2.17 (m, 1H), 1.98-2.04 (m, 2H), 1.88 (br m., 2H), 1.75-1.82 (m, 4H), 1.50-1.57 (m, 2H) ppm (amide NH, alcohol OH and pyridylamine NH not detected).

Example 9

3-(4,6-Dimethyl-pyrimidin-2-ylamino)-N-[(E)-5-hydroxy-adamantan-2-yl]-benzamide

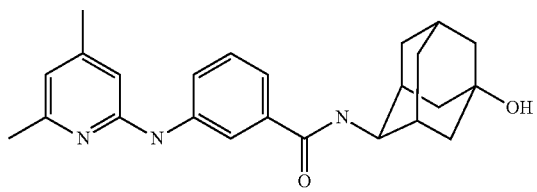 [SMILES: Cc1cc(C)nc(Nc2cccc(C(=O)NC3C4CC5CC3CC(O)(C5)C4)c2)c1]

A solution of 3-(4,6-dimethyl-pyrimidin-2-ylamino)-benzoic acid (100 mg, 0.41 mmol), (E)-4-amino-adamantan-1-ol.hydrochloride (90 mg, 0.45 mmol), HBTU (170 mg, 0.45 mmol), diisopropylethyl amine (0.14 ml, 0.8 mmol) in DMF (1.0 mL) was stirred at room temperature for 1 h. Water was added and product was extracted with ethyl acetate. Crude product was purified by flash column chromatography using 20% hexanes in ethyl acetate using a prepacked silica column to obtain 3-(4,6-dimethyl-pyrimidin-2-ylamino)-N-[(E)-5-hydroxy-adamantan-2-yl]-benzamide (55 mg).

LC-MS (m/z): 394.04 (M+1)+; 1H NMR (400 MHz, CD3OD): δ 8.32 (s, 1H), 7.70-7.75 (m, 1H), 7.33-7.38 (m, 2H), 6.61 (s, 1H), 4.06-4.10 (m, 1H), 2.35 (s, 6H), 2.24 (br s., 2H), 2.11-2.17 (m, 1H), 2.00-2.08 (m, 2H), 1.89 (br s, 2H), 1.75-1.83 (m, 4H), 1.49-1.57 (m, 2H) ppm (amide NH, alcohol OH and pyrimidinyl amine NH not detected).

Biological Assays

Protocol for in vitro 11β-HSD Assay

Materials Needed:

96 well ½ area well plate (Fisher #07-200-329)

CISBIO Cortisol kit #62CO2PEB

Buffers:

Assay Buffer: (water based) used for Enzyme, Compounds and Microsomes: 20 mM Tris, 5 mM EDTA, and pH 6.0.

Enzyme Buffer: 333 μM NADPH (FAC 200 μM) and 266 nM Cortisone (FAC 160 nM).

Protocol:

1) Test compounds (10 mM stock in 100% DMSO) were diluted in Assay Buffer (see below) with 1% DMSO FAC and placed into the 96-well plate. Test compounds were typically tested over 10 concentrations (30 μM-0.3 nM).

2) 30 μL Enzyme Buffer, 10 μL Test Compound, 10 μL human microsomes were added to the test compounds and mixed gently by tapping the plate.

3) The plates were incubated for 2 h at 37° C.

4) 25 μL anti Cortisol-K and 25 μL Cortisol d2 were added to the plate and mixed gently by tapping the plate.

5) The plates were incubated at room temperature for 2 h.

6) The plates were read on an Envision model 2120 Perkin-Elmer using emission filters #205 and #217. Data is calculated as a change in delta F. The results are summarized in Table 2, below.

TABLE 2

| Example | in vitro 11β-HSD Assay [EC50 (nm)] |
|---------|-----------------------------------|
| 1 | <200 |
| 2 | <200 |
| 3 | <200 |
| 4 | <500 |
| 5 | <3000 |
| 6 | <200 |
| 7 | <200 |
| 8 | <200 |
| 9 | <500 |

Human Adipocytes Cell Based Assay

Cells were ordered from ZenBio, RTP, NC (www.zenbio.com (OA-1096-3)) pre-plated (96 well). Cell Media was supplied by ZenBio (Omental Adipocyte Medium #OM-AM).

Test compounds were prepared at 10 concentrations (10 uM -0.1 nM). Dilutions were made up in Cell Media. Cell Media from the plate is aspirated and 97 μL was added to the wells.

The plates were incubated for 15 minutes (37° C.).

3 μL of 10 mM cortisone (Sigma #C2755) (300 nM FAC) was added, for a total well volume of 100 μL.

The plates were incubated for 24 hours (37° C.).

The media was harvested from cells.

The samples were then assayed using Cortisol ELISA Kits (R & D Systems #SKGE008). Samples were diluted by a factor of 5. Specific instructions were included in the kit to quantify presence of cortisol in samples through an ELISA assay.

The plates were read on a Spectramax at 450 nm OD.

The IC50 values for select test compounds was <300 nm.

While the invention has been described and illustrated with reference to certain embodiments thereof, those skilled in the art will appreciate that various changes, modifications and substitutions can be made therein without departing from the spirit and scope of the invention. For example, effective dosages other than the dosages as set forth herein may be applicable as a consequence of variations in the responsiveness of the mammal being treated. Likewise, the specific pharmacological responses observed may vary according to and depending on the particular active compound selected or whether there are present pharmaceutical carriers, as well as the type of formulation and mode of administration employed, and such expected variations or differences in the results are contemplated in accordance with the objects and practices of the present invention.

We claim:

1. A compound, which is:
3-(5-chloro-pyridin-2-yloxy)-N-(5-hydroxy-adamantan-2-yl)-benzamide;
N-(5-hydroxy-adamantan-2-yl)-3-(5-trifluoromethyl-pyridin-2-yloxy)-benzamide;
3-(5-chloro-pyridin-2-ylsulfanyl)-N-(5-hydroxy-adamantan-2-yl)-benzamide;
3-(5-chloro-pyridine-2-sulfinyl)-N-(5-hydroxy-adamantan-2-yl)-benzamide;
3-(5-chloro-pyridine-2-sulfonyl)-N-(5-hydroxy-adamantan-2-yl)-benzamide;
3-(6-chloro-pyridazin-3-yloxy)-N-(5-hydroxy-adamantan-2-yl)-benzamide;
3-(3,5-dichloro-pyridin-2-yloxy)-N-(5-hydroxy-adamantan-2-yl)-benzamide;
3-(4,6-dimethyl-pyrimidin-2-ylamino)-N-(5-hydroxy-adamantan-2-yl)-benzamide;
or a pharmaceutically acceptable salt of any of the foregoing;
where with respect to the E- and Z-isomers of the compound, at least 90% of the compound is in the form of the E-isomer.

2. The compound of claim 1, where at least 95% of the compound is in the form of the E-isomer.

3. The compound of claim 1, where at least 98% of the compound is in the form of the E-isomer.

4. A compound, which is 3-(5-chloro-pyridin-2-yloxy)-N-(5-hydroxy-adamantan-2-yl)-benzamide or a pharmaceutically acceptable salt thereof, where with respect to the E- and Z-isomers of the compound, at least 90% of the compound is in the form of the E-isomer.

5. The compound of claim 4, where at least 95% of the compound is in the form of the E-isomer.

6. The compound of claim 4, where at least 98% of the compound is in the form of the E-isomer.

7. The compound of claim 4, where the compound is 3-(5-chloro-pyridin-2-yloxy)-N-(5-hydroxy-adamantan-2-yl)-benzamide.

8. The compound of claim 7, where at least 95% of the compound is in the form of the E-isomer.

9. The compound of claim 7, where at least 98% of the compound is in the form of the E-isomer.

10. The compound of claim 4, where the compound is a pharmaceutically acceptable salt of 3-(5-chloro-pyridin-2-yloxy)-N-(5-hydroxy-adamantan-2-yl)-benzamide.

11. The compound of claim 10, where at least 95% of the compound is in the form of the E-isomer.

12. The compound of claim 10, where at least 98% of the compound is in the form of the E-isomer.

13. A compound, which is N-(5-hydroxy-adamantan-2-yl)-3-(5-trifluoromethyl-pyridin-2-yloxy)-benzamide or a pharmaceutically acceptable salt thereof, where with respect to the E- and Z-isomers of the compound, at least 90% of the compound is in the form of the E-isomer.

14. The compound of claim 13, where at least 95% of the compound is in the form of the E-isomer.

15. The compound of claim 13, where at least 98% of the compound is in the form of the E-isomer.

16. The compound of claim 13, where the compound is N-(5-hydroxy-adamantan-2-yl)-3-(5-trifluoromethyl-pyridin-2-yloxy)-benzamide.

17. The compound of claim 16, where at least 95% of the compound is in the form of the E-isomer.

18. The compound of claim 16, where at least 98% of the compound is in the form of the E-isomer.

19. The compound of claim 13, where the compound is a pharmaceutically acceptable salt of N-(5-hydroxy-adamantan-2-yl)-3-(5-trifluoromethyl-pyridin-2-yloxy)-benzamide.

20. The compound of claim 19, where at least 95% of the compound is in the form of the E-isomer.

21. The compound of claim 19, where at least 98% of the compound is in the form of the E-isomer.

22. A compound, which is 3-(5-chloro-pyridin-2-ylsulfanyl)-N-(5-hydroxy-adamantan-2-yl)-benzamide or a pharmaceutically acceptable salt thereof, where with respect to the E- and Z-isomers of the compound, at least 90% of the compound is in the form of the E-isomer.

23. The compound of claim 22, where at least 95% of the compound is in the form of the E-isomer.

24. The compound of claim 22, where at least 98% of the compound is in the form of the E-isomer.

25. The compound of claim 22, where the compound is 3-(5-chloro-pyridin-2-ylsulfanyl)-N-(5-hydroxy-adamantan-2-yl)-benzamide.

26. The compound of claim 25, where at least 95% of the compound is in the form of the E-isomer.

27. The compound of claim 25, where at least 98% of the compound is in the form of the E-isomer.

28. The compound of claim 22, where the compound is a pharmaceutically acceptable salt of 3-(5-chloro-pyridin-2-ylsulfanyl)-N-(5-hydroxy-adamantan-2-yl)-benzamide.

29. The compound of claim 28, where at least 95% of the compound is in the form of the E-isomer.

30. The compound of claim 28, where at least 98% of the compound is in the form of the E-isomer.

31. A compound, which is 3-(6-chloro-pyridazin-3-yloxy)-N-(5-hydroxy-adamantan-2-yl)-benzamide or a pharmaceutically acceptable salt thereof, where with respect to the E- and Z-isomers of the compound, at least 90% of the compound is in the form of the E-isomer.

32. The compound of claim 31, where at least 95% of the compound is in the form of the E-isomer.

33. The compound of claim 31, where at least 98% of the compound is in the form of the E-isomer.

34. The compound of claim 31, where the compound is 3-(6-chloro-pyridazin-3-yloxy)-N-(5-hydroxy-adamantan-2-yl)-benzamide.

35. The compound of claim 34, where at least 95% of the compound is in the form of the E-isomer.

36. The compound of claim 34, where at least 98% of the compound is in the form of the E-isomer.

37. The compound of claim 31, where the compound is a pharmaceutically acceptable salt of 3-(6-chloro-pyridazin-3-yloxy)-N-(5-hydroxy-adamantan-2-yl)-benzamide.

38. The compound of claim 37, where at least 95% of the compound is in the form of the E-isomer.

39. The compound of claim 37, where at least 98% of the compound is in the form of the E-isomer.

40. A compound, which is 3-(3,5-dichloro-pyridin-2-yloxy)-N-(5-hydroxy-adamantan-2-yl)-benzamide or a pharmaceutically acceptable salt thereof, where with respect to the E- and Z-isomers of the compound, at least 90% of the compound is in the form of the E-isomer.

41. The compound of claim 40, where at least 95% of the compound is in the form of the E-isomer.

42. The compound of claim 40, where at least 98% of the compound is in the form of the E-isomer.

43. The compound of claim 40, where the compound is 3-(3,5-dichloro-pyridin-2-yloxy)-N-(5-hydroxy-adamantan-2-yl)-benzamide.

44. The compound of claim 43, where at least 95% of the compound is in the form of the E-isomer.

45. The compound of claim 43, where at least 98% of the compound is in the form of the E-isomer.

46. The compound of claim 40, where the compound is a pharmaceutically acceptable salt of 3-(3,5-dichloro-pyridin-2-yloxy)-N-(5-hydroxy-adamantan-2-yl)-benzamide.

47. The compound of claim 46, where at least 95% of the compound is in the form of the E-isomer.

48. The compound of claim 46, where at least 98% of the compound is in the form of the E-isomer.

49. A compound, which is 3-(4,6-dimethyl-pyrimidin-2-ylamino)-N-(5-hydroxy-adamantan-2-yl)-benzamide or a pharmaceutically acceptable salt thereof, where with respect to the E- and Z-isomers of the compound, at least 90% of the compound is in the form of the E-isomer.

50. The compound of claim 49, where at least 95% of the compound is in the form of the E-isomer.

51. The compound of claim 49, where at least 98% of the compound is in the form of the E-isomer.

52. The compound of claim 49, where the compound is 3-(4,6-dimethyl-pyrimidin-2-ylamino)-N-(5-hydroxy-adamantan-2-yl)-benzamide.

53. The compound of claim 52, where at least 95% of the compound is in the form of the E-isomer.

54. The compound of claim 52, where at least 98% of the compound is in the form of the E-isomer.

55. The compound of claim 49, where the compound is a pharmaceutically acceptable salt of 3-(4,6-dimethyl-pyrimidin-2-ylamino)-N-(5-hydroxy-adamantan-2-yl)-benzamide.

56. The compound of claim 55, where at least 95% of the compound is in the form of the E-isomer.

57. The compound of claim 55, where at least 98% of the compound is in the form of the E-isomer.

58. A pharmaceutical composition comprising a compound and a pharmaceutically acceptable carrier or excipient, where the compound is:
   3-(5-chloro-pyridin-2-yloxy)-N-(5-hydroxy-adamantan-2-yl)-benzamide;
   N-(5-hydroxy-adamantan-2-yl)-3-(5-trifluoromethyl-pyridin-2-yloxy)-benzamide;
   3-(5-chloro-pyridin-2-ylsulfanyl)-N-(5-hydroxy-adamantan-2-yl)-benzamide;
   3-(5-chloro-pyridine-2-sulfinyl)-N-(5-hydroxy-adamantan-2-yl)-benzamide;
   3-(5-chloro-pyridine-2-sulfonyl)-N-(5-hydroxy-adamantan-2-yl)-benzamide;
   3-(6-chloro-pyridazin-3-yloxy)-N-(5-hydroxy-adamantan-2-yl)-benzamide;
   3-(3,5-dichloro-pyridin-2-yloxy)-N-(5-hydroxy-adamantan-2-yl)-benzamide;
   3-(4,6-dimethyl-pyrimidin-2-ylamino)-N-(5-hydroxy-adamantan-2-yl)-benzamide;
   or a pharmaceutically acceptable salt of any of the foregoing;
   where with respect to the E- and Z-isomers of the compound at least 90% of the compound present in the composition is in the form of the E-isomer.

59. The composition of claim 58, where at least 95% of the compound present in the composition is in the form of the E-isomer.

60. The composition of claim 58, where at least 98% of the compound present in the composition is in the form of the E-isomer.

61. A pharmaceutical composition comprising a compound of claim 4 and a pharmaceutically acceptable carrier or excipient.

62. A pharmaceutical composition comprising a compound of claim 13 and a pharmaceutically acceptable carrier or excipient.

63. A pharmaceutical composition comprising a compound of claim 22 and a pharmaceutically acceptable carrier or excipient.

* * * * *